United States Patent
Libbus et al.

(10) Patent No.: US 10,893,813 B2
(45) Date of Patent: *Jan. 19, 2021

(54) HEART FAILURE MANAGEMENT

(71) Applicant: Cardiac Pacemakers, Inc., St. Paul, MN (US)

(72) Inventors: Imad Libbus, St. Paul, MN (US); Krzysztof Z. Siejko, Maple Grove, MN (US); Marina V. Brockway, Shoreview, MN (US); Robert J. Sweeney, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/879,139

(22) Filed: Jan. 24, 2018

(65) Prior Publication Data
US 2018/0146863 A1   May 31, 2018

Related U.S. Application Data

(63) Continuation of application No. 15/608,692, filed on May 30, 2017, now Pat. No. 9,924,877, which is a (Continued)

(51) Int. Cl.
*A61B 5/0205* (2006.01)
*A61N 1/36* (2006.01)
(Continued)

(52) U.S. Cl.
CPC .......... *A61B 5/0205* (2013.01); *A61B 5/0031* (2013.01); *A61B 5/0215* (2013.01);
(Continued)

(58) Field of Classification Search
CPC .............. A51N 1/36114; A51N 1/3627; A51N 1/36514; A51N 1/36117
See application file for complete search history.

(56) References Cited

U.S. PATENT DOCUMENTS

| | | | |
|---|---|---|---|
| 4,202,340 A | 5/1980 | Langer et al. | |
| 4,905,706 A | 3/1990 | Duff et al. | |

(Continued)

FOREIGN PATENT DOCUMENTS

| | | |
|---|---|---|
| AU | 2007342523 B2 | 7/2008 |
| EP | 1505816 A1 | 2/2005 |

(Continued)

OTHER PUBLICATIONS

"U.S. Appl. No. 11/382,128, Final Office Action dated Mar. 30, 2010", 9 pgs.

(Continued)

*Primary Examiner* — Paula J Stice
(74) *Attorney, Agent, or Firm* — Schwegman Lundberg & Woessner, P.A

(57) ABSTRACT

Various system embodiments comprise a stimulator adapted to deliver a stimulation signal for a heart failure therapy, a number of sensors adapted to provide at least a first measurement of a heart failure status and a second measurement of the heart failure status, and a controller. The controller is connected to the stimulator and to the number of sensors. The controller is adapted to use the first and second measurements to create a heart failure status index, and control the stimulator to modulate the signal using the index. Other aspects and embodiments are provided herein.

20 Claims, 15 Drawing Sheets

Related U.S. Application Data continuation of application No. 14/644,841, filed on Mar. 11, 2015, now Pat. No. 9,669,218, which is a continuation of application No. 14/143,492, filed on Dec. 30, 2013, now Pat. No. 8,996,107, which is a continuation of application No. 13/731,691, filed on Dec. 31, 2012, now Pat. No. 8,620,427, which is a continuation of application No. 13/214,564, filed on Aug. 22, 2011, now Pat. No. 8,346,360, which is a continuation of application No. 11/382,128, filed on May 8, 2006, now Pat. No. 8,005,543.

(51) Int. Cl.
| | |
|---|---|
| A61N 1/365 | (2006.01) |
| A61B 7/00 | (2006.01) |
| A61N 1/362 | (2006.01) |
| A61B 5/00 | (2006.01) |
| A61B 5/0215 | (2006.01) |
| A61B 5/0402 | (2006.01) |
| A61B 5/0488 | (2006.01) |
| A61N 1/372 | (2006.01) |
| A61B 7/04 | (2006.01) |

(52) U.S. Cl.
CPC ........ *A61B 5/02158* (2013.01); *A61B 5/0402* (2013.01); *A61B 5/0488* (2013.01); *A61B 7/00* (2013.01); *A61N 1/3627* (2013.01); *A61N 1/36114* (2013.01); *A61N 1/36128* (2013.01); *A61N 1/36139* (2013.01); *A61N 1/36514* (2013.01); *A61N 1/36564* (2013.01); *A61N 1/36585* (2013.01); *A61N 1/372* (2013.01); *A61B 7/04* (2013.01); *A61N 1/36117* (2013.01); *A61N 1/36521* (2013.01); *A61N 1/36542* (2013.01); *A61N 1/36578* (2013.01); *A61N 1/36592* (2013.01); *A61N 1/37288* (2013.01)

(56) References Cited

U.S. PATENT DOCUMENTS

| | | | |
|---|---|---|---|
| 4,981,139 | A | 1/1991 | Pfohl |
| 5,010,889 | A | 4/1991 | Bredesen et al. |
| 5,025,809 | A | 6/1991 | Johnson et al. |
| 5,218,969 | A | 6/1993 | Bredesen et al. |
| 5,330,505 | A | 7/1994 | Cohen |
| 5,330,507 | A | 7/1994 | Schwartz |
| 5,337,752 | A | 8/1994 | Reeves |
| 5,674,256 | A | 10/1997 | Carlson |
| 5,718,235 | A | 2/1998 | Golosarsky et al. |
| 5,772,996 | A | 6/1998 | Atkinson et al. |
| 5,788,643 | A | 8/1998 | Feldman |
| 5,860,933 | A | 1/1999 | Don Michael |
| 5,916,239 | A | 6/1999 | Geddes et al. |
| 6,059,724 | A | 5/2000 | Campell et al. |
| 6,178,349 | B1 | 1/2001 | Kieval |
| 6,243,606 | B1 | 6/2001 | Mann et al. |
| 6,246,910 | B1 | 6/2001 | Bonnet et al. |
| 6,272,377 | B1 | 8/2001 | Sweeney et al. |
| 6,351,675 | B1 | 2/2002 | Tholen et al. |
| 6,438,408 | B1 | 8/2002 | Mulligan et al. |
| 6,459,929 | B1 | 10/2002 | Hopper et al. |
| 6,527,729 | B1 | 3/2003 | Turcott |
| 6,645,153 | B2 | 11/2003 | Kroll et al. |
| 6,821,249 | B2 | 11/2004 | Casscells, III et al. |
| 6,980,851 | B2 | 12/2005 | Zhu et al. |
| 7,020,521 | B1 | 3/2006 | Brewer et al. |
| 7,062,314 | B2 | 6/2006 | Zhu et al. |
| 7,115,096 | B2 | 10/2006 | Siejko et al. |
| 7,123,961 | B1 | 10/2006 | Kroll et al. |
| 7,123,962 | B2 | 10/2006 | Siejko et al. |
| 7,155,277 | B1 | 12/2006 | Brewer et al. |
| 7,226,422 | B2 | 6/2007 | Hatlestsad et al. |
| 7,248,923 | B2 | 7/2007 | Maile et al. |
| 7,277,761 | B2 | 10/2007 | Shelchuk |
| 7,387,610 | B2 | 6/2008 | Stahmann et al. |
| 7,399,277 | B2 | 7/2008 | Saidara et al. |
| 7,400,928 | B2 | 7/2008 | Hatlestsad |
| 7,413,549 | B1 | 8/2008 | Koh |
| 7,424,321 | B2 | 9/2008 | Wariar et al. |
| 7,431,699 | B2 | 10/2008 | Siejko et al. |
| 7,559,901 | B2 | 7/2009 | Maile et al. |
| 7,582,061 | B2 | 9/2009 | Li et al. |
| 7,629,889 | B2 | 12/2009 | Sachanandani et al. |
| 7,662,104 | B2 | 2/2010 | Siejko et al. |
| 7,713,213 | B2 | 5/2010 | Siejko et al. |
| 7,778,708 | B1 | 8/2010 | Koh et al. |
| 7,853,327 | B2 | 12/2010 | Patangay et al. |
| 7,922,669 | B2 | 4/2011 | Zhang et al. |
| 8,005,543 | B2 | 8/2011 | Libbus et al. |
| 8,031,076 | B2 | 10/2011 | Sachanandani et al. |
| 8,211,033 | B2 | 7/2012 | Siejko et al. |
| 8,223,023 | B2 | 7/2012 | Sachanandani et al. |
| 8,257,271 | B2 | 9/2012 | Siejko et al. |
| 8,346,360 | B2 | 1/2013 | Libbus et al. |
| 8,620,427 | B2 | 12/2013 | Libbus et al. |
| 8,996,107 | B2 | 3/2015 | Libbus et al. |
| 9,669,218 | B2 | 6/2017 | Libbus et al. |
| 9,924,877 | B2 | 3/2018 | Libbus et al. |
| 2002/0016550 | A1 | 2/2002 | Sweeney et al. |
| 2002/0107553 | A1 | 8/2002 | Hill et al. |
| 2003/0055461 | A1 | 3/2003 | Girouard et al. |
| 2003/0060851 | A1 | 3/2003 | Kramer et al. |
| 2003/0092975 | A1 | 5/2003 | Casscells, III et al. |
| 2003/0149453 | A1* | 8/2003 | Kroll ............... A61N 1/36514 607/17 |
| 2003/0158492 | A1 | 8/2003 | Sheldon et al. |
| 2004/0106960 | A1 | 6/2004 | Siejko et al. |
| 2004/0106961 | A1 | 6/2004 | Siejko et al. |
| 2004/0122484 | A1 | 6/2004 | Hatlestad et al. |
| 2004/0122485 | A1 | 6/2004 | Stahmann et al. |
| 2004/0127792 | A1 | 7/2004 | Siejko et al. |
| 2004/0133080 | A1 | 7/2004 | Mazar |
| 2004/0133247 | A1 | 7/2004 | Stahmann et al. |
| 2004/0172080 | A1 | 9/2004 | Stadler et al. |
| 2004/0186525 | A1* | 9/2004 | Burnes ............... A61B 5/02405 607/17 |
| 2005/0004485 | A1 | 1/2005 | Crosby et al. |
| 2005/0059897 | A1 | 3/2005 | Snell et al. |
| 2005/0065555 | A1 | 3/2005 | Er |
| 2005/0131469 | A1 | 6/2005 | Cohen |
| 2005/0143633 | A1 | 6/2005 | Jelliffe et al. |
| 2005/0148896 | A1 | 7/2005 | Siejko et al. |
| 2005/0149136 | A1 | 7/2005 | Siejko et al. |
| 2005/0187789 | A1 | 8/2005 | Hatlestad et al. |
| 2005/0192637 | A1 | 9/2005 | Girouard et al. |
| 2005/0234356 | A1 | 10/2005 | Rowlandson et al. |
| 2006/0010090 | A1 | 1/2006 | Brockway et al. |
| 2006/0025931 | A1 | 2/2006 | Rosen et al. |
| 2006/0030890 | A1 | 2/2006 | Cosentino et al. |
| 2006/0058966 | A1 | 3/2006 | Bruckner et al. |
| 2006/0089679 | A1 | 4/2006 | Zhu et al. |
| 2006/0094967 | A1 | 5/2006 | Bennett et al. |
| 2006/0161070 | A1 | 7/2006 | Siejko et al. |
| 2006/0241510 | A1 | 10/2006 | Halperin et al. |
| 2006/0241513 | A1 | 10/2006 | Hatlestad et al. |
| 2006/0270939 | A1 | 11/2006 | Wariar et al. |
| 2006/0271116 | A1 | 11/2006 | Stahmann et al. |
| 2006/0282000 | A1 | 12/2006 | Zhang et al. |
| 2007/0078491 | A1 | 4/2007 | Siejko et al. |
| 2007/0142732 | A1 | 6/2007 | Brockway et al. |
| 2007/0213599 | A1 | 9/2007 | Siejko et al. |
| 2007/0260284 | A1* | 11/2007 | Pastore ............... A61N 1/36114 607/9 |
| 2007/0260285 | A1 | 11/2007 | Libbus et al. |
| 2008/0157980 | A1 | 7/2008 | Sachanandani et al. |
| 2008/0161651 | A1 | 7/2008 | Peterson et al. |
| 2008/0161700 | A1 | 7/2008 | Sachanandani et al. |
| 2008/0162182 | A1 | 7/2008 | Cazares et al. |
| 2008/0162183 | A1 | 7/2008 | Sachanandani et al. |
| 2009/0018461 | A1 | 1/2009 | Siejko et al. |

(56) References Cited

U.S. PATENT DOCUMENTS

| | | | |
|---|---|---|---|
| 2009/0069708 | A1 | 3/2009 | Hatlestad et al. |
| 2009/0287106 | A1 | 11/2009 | Zhang et al. |
| 2010/0045467 | A1 | 2/2010 | Sachanandani et al. |
| 2010/0222653 | A1 | 9/2010 | Siejko et al. |
| 2011/0077543 | A1 | 3/2011 | Patangay et al. |
| 2011/0098588 | A1 | 4/2011 | Siejko et al. |
| 2011/0301660 | A1 | 12/2011 | Libbus et al. |
| 2011/0319726 | A1 | 12/2011 | Sachanandani et al. |
| 2013/0123873 | A1 | 5/2013 | Libbus et al. |
| 2014/0114370 | A1 | 4/2014 | Libbus et al. |
| 2015/0182750 | A1 | 7/2015 | Libbus et al. |
| 2017/0258337 | A1 | 9/2017 | Libbus et al. |

FOREIGN PATENT DOCUMENTS

| | | |
|---|---|---|
| EP | 1604705 A1 | 12/2005 |
| EP | 2021070 B1 | 5/2012 |
| JP | 2001511680 A | 8/2001 |
| JP | 2006523120 A | 10/2006 |
| WO | WO-04060483 A1 | 7/2004 |
| WO | WO-2004084991 A1 | 10/2004 |
| WO | WO-2005110213 A2 | 11/2005 |
| WO | WO-2006026383 A2 | 3/2006 |
| WO | WO-2006127594 A2 | 11/2006 |
| WO | WO-2007133873 A2 | 11/2007 |
| WO | WO-2007133873 A3 | 11/2007 |
| WO | WO-2008085308 A1 | 7/2008 |
| WO | WO-2008085309 A1 | 7/2008 |
| WO | WO-2009035596 A1 | 3/2009 |

OTHER PUBLICATIONS

"U.S. Appl. No. 11/382,128, Non-Final Office Action dated Sep. 1, 2010", 12 pgs.

"U.S. Appl. No. 11/382,128, Non-Final Office Action dated Oct. 28, 2009", 11 pgs.

"U.S. Appl. No. 11/382,128, Notice of Allowance dated Apr. 11, 2011", 9 pgs.

"U.S. Appl. No. 11/382,128, Preliminary Amendment filed Apr. 12, 2007", 8 pgs.

"U.S. Appl. No. 11/382,128, Response filed Jan. 28, 2010 to Non Final Office Action dated Oct. 28, 2009", 10 pgs.

"U.S. Appl. No. 11/382,128, Response filed Mar. 1, 2011 to Non Final Office Action dated Sep. 1, 2010", 14 pgs.

"U.S. Appl. No. 11/382,128, Response filed Jul. 15, 2009 to Restriction Requirement dated Jun. 15, 2009", 12 pgs.

"U.S. Appl. No. 11/382,128, Response filed Jul. 29, 2010 to Final Office Action dated Mar. 30, 2010", 13 pgs.

"U.S. Appl. No. 11/382,128, Restriction Requirement dated Jun. 15, 2009", 11 pgs.

"U.S. Appl. No. 13/214,564, Notice of Allowance dated Sep. 4, 2012", 9 pgs.

"U.S. Appl. No. 13/214,564, Response filed Aug. 21, 2012 to Restriction Requirement dated Jul. 24, 2012", 12 pgs.

"U.S. Appl. No. 13/214,564, Restriction Requirement dated Jul. 24, 2012", 7 pgs.

"U.S. Appl. No. 13/731,691, Notice of Allowance dated Aug. 20, 2013", 9 pgs.

"U.S. Appl. No. 13/731,691, Response filed Jun. 13, 2013 to Restriction Requirement dated May 14, 2013", 7 pgs.

"U.S. Appl. No. 13/731,691, Restriction Requirement dated May 14, 2013", 6 pgs.

"U.S. Appl. No. 14/143,492, Non Final Office Action dated Aug. 14, 2014", 9 pgs.

"U.S. Appl. No. 14/143,492, Notice of Allowance dated Nov. 24, 2014", 9 pgs.

"U.S. Appl. No. 14/143,492, Response filed Jul. 28, 2014 to Restriction Requirement dated Jun. 2, 2014", 8 pgs.

"U.S. Appl. No. 14/143,492, Response filed Nov. 11, 2014 to Non Final Office Action dated Aug. 14, 2014", 11 pgs.

"U.S. Appl. No. 14/143,492, Restriction Requirement dated Jun. 2, 2014", 7 pgs.

"U.S. Appl. No. 14/644,841, Advisory Action dated May 2, 2016", 3 pgs.

"U.S. Appl. No. 14/644,841, Examiner Interview Summary dated Apr. 19, 2016", 3 pgs.

"U.S. Appl. No. 14/644,841, Final Office Action dated Feb. 18, 2016", 13 pgs.

"U.S. Appl. No. 14/644,841, Final Office Action dated Oct. 13, 2016", 11 pgs.

"U.S. Appl. No. 14/644,841, Non Final Office Action dated Jun. 29, 2016", 13 pgs.

"U.S. Appl. No. 14/644,841, Non Final Office Action dated Sep. 10, 2015", 12 pgs.

"U.S. Appl. No. 14/644,841, Notice of Allowance dated Feb. 2, 2017", 7 pgs.

"U.S. Appl. No. 14/644,841, Preliminary Amendment filed Mar. 12, 2015", 5 pgs.

"U.S. Appl. No. 14/644,841, Response filed Jan. 13, 2017 to Final Office Action dated Oct. 13, 2016", 9 pgs.

"U.S. Appl. No. 14/644,841, Response filed Apr. 18, 2016 to Final Office Action dated Feb. 18, 2016", 9 pgs.

"U.S. Appl. No. 14/644,841, Response filed Sep. 29, 2016 to Non Final Office Action dated Jun. 29, 2016", 9 pgs.

"U.S. Appl. No. 14/644,841, Response filed Dec. 7, 2015 to Non Final Office Action dated Sep. 10, 2015", 13 pgs.

"U.S. Appl. No. 15/608,692, Non Final Office Action dated Jul. 13, 2017", 12 pgs.

"U.S. Appl. No. 15/608,692, Notice of Allowance dated Nov. 13, 2017", 8 pgs.

"U.S. Appl. No. 15/608,692, Preliminary Amendment filed May 31, 2017", 6 pgs.

"U.S. Appl. No. 15/608,692, Response filed Oct. 11, 2017 to Non Final Office Action dated Jul. 13, 2017", 11 pgs.

"European Application Serial No. 07760574.9, Office Action dated May 29, 2009", 5 pgs.

"European Application Serial No. 07760574.9, Response filed Sep. 20, 2011 to Summons to Attend Oral Proceedings dated Jul. 8, 2011", 14 pgs.

"European Application Serial No. 07760574.9, Summon to attend Oral Proceeding dated Jul. 8, 2011", 8 pgs.

"International Application Serial No. PCT/US2007/066543, International Search Report dated Nov. 30, 2007", 5 pgs.

"International Application Serial No. PCT/US2007/066543, Written Opinion dated Nov. 30, 2007", 8 pgs.

"Japanese Application Serial No. 2009-509916, Office Action dated Feb. 8, 2012", (W/ English Translation), 5 pgs.

"Japanese Application Serial No. 2009-509916, Response filed May 2, 2012 to Office Action dated Mar. 6, 2012", (W/ English Translation of Claims), 12 pgs.

"U.S. Appl. No. 10/746,853, Final Office Action dated May 22, 2007", 11 pgs.

"U.S. Appl. No. 10/746,853, Non-Final Office Action dated Sep. 26, 2007", 8 pgs.

"U.S. Appl. No. 10/746,853, Non-Final Office Action dated Dec. 19, 2006", 10 pgs.

"U.S. Appl. No. 10/746,853, Notice of Allowance dated May 30, 2008", 4 pgs.

"U.S. Appl. No. 10/746,853, Response filed Jan. 17, 2008 to Non-Final Office Action dated Sep. 26, 2007", 18 pgs.

"U.S. Appl. No. 10/746,853, Response filed Mar. 15, 2007 to Non-Final Office Action dated Dec. 19, 2006", 16 pgs.

"U.S. Appl. No. 10/746,853, Response filed Jul. 23, 2007 to Final Office Action dated May 22, 2007", 16 pgs.

"U.S. Appl. No. 11/276,735, Examiner Interview Summary dated Aug. 5, 2009", 4 pgs.

"U.S. Appl. No. 11/276,735, Non Final Office Action dated May 7, 2009", 8 pgs.

"U.S. Appl. No. 11/276,735, Notice of Allowance dated Dec. 29, 2009", 6 pgs.

"U.S. Appl. No. 11/276,735, Response filed Feb. 9, 2009 to Restriction Requirement dated Dec. 8, 2008", 12 pgs.

(56) References Cited

OTHER PUBLICATIONS

"U.S. Appl. No. 11/276,735, Response filed Aug. 7, 2009 to Non Final Office Action dated May 7, 2009", 18 pgs.
"U.S. Appl. No. 11/276,735, Restriction Requirement dated Dec. 8, 2008", 7 pgs.
"U.S. Appl. No. 11/382,128, Preliminary Amendment filed Mar. 12, 2015", 5 pgs.
"U.S. Appl. No. 11/465,878, Issue Notification dated Jun. 15, 2012", 1 pg.
"U.S. Appl. No. 11/465,878, Notice of Allowance dated Mar. 5, 2012", 7 pgs.
"U.S. Appl. No. 12/283,760, Final Office Action dated Apr. 24, 2012", 16 pgs.
"U.S. Appl. No. 12/283,760, Non Final Office Action dated Oct. 5, 2011", 9 pgs.
"U.S. Appl. No. 12/283,760, Response filed Feb. 6, 2012 to Non Final Office Action dated Oct. 5, 2011", 15 pgs.
"U.S. Appl. No. 12/776,557, Corrected Notice of Allowability dated Jul. 12, 2012", 4 pgs.
"U.S. Appl. No. 12/776,557, Non Final Office Action dated Jan. 19, 2012", 6 pgs.
"U.S. Appl. No. 12/776,557, Notice of Allowance dated May 11, 2012", 7 pgs.
"U.S. Appl. No. 12/776,557, Response filed Apr. 9, 2012 to Non Final Office Action dated Jan. 19, 2012", 9 pgs.
"U.S. Appl. No. 12/776,557, Response filed Dec. 27, 2011 to Restriction Requirement dated Nov. 28, 2011", 13 pgs.
"U.S. Appl. No. 12/776,557, Restriction Requirement dated Nov. 28, 2011", 7 pgs.
"U.S. Appl. No. 13/229,110, Notice of Allowance dated Mar. 20, 2012", 5 pgs.
"U.S. Appl. No. 13/229,110, Response filed Mar. 2, 2012 to Non Final Office Action dated Dec. 5, 2011", 9 pgs.
"European Application Serial No. 07862948.2, Response filed Apr. 30, 2012 to Office Action dated Dec. 19, 2011", 19 pgs.
Makhoul, John, "Linear Prediction: A Tutorial Review", Proceedings of the IEEE, 63, (Apr. 1975), 561-580.
Rohling, H., "Radar CFAR Thresholding in Clutter and Multiple Target Situations", IEEE Trans. Aerosp. Electron. Syst., vol.AES-19, No. 4, (Jul. 1983), 608-621.
Rohling, H., "Some radar topics: waveform design, range CFAR and target recognition", NATO Advanced Study Institute, Advances in Sensing with Security Applications, (2005), 1-30.

\* cited by examiner

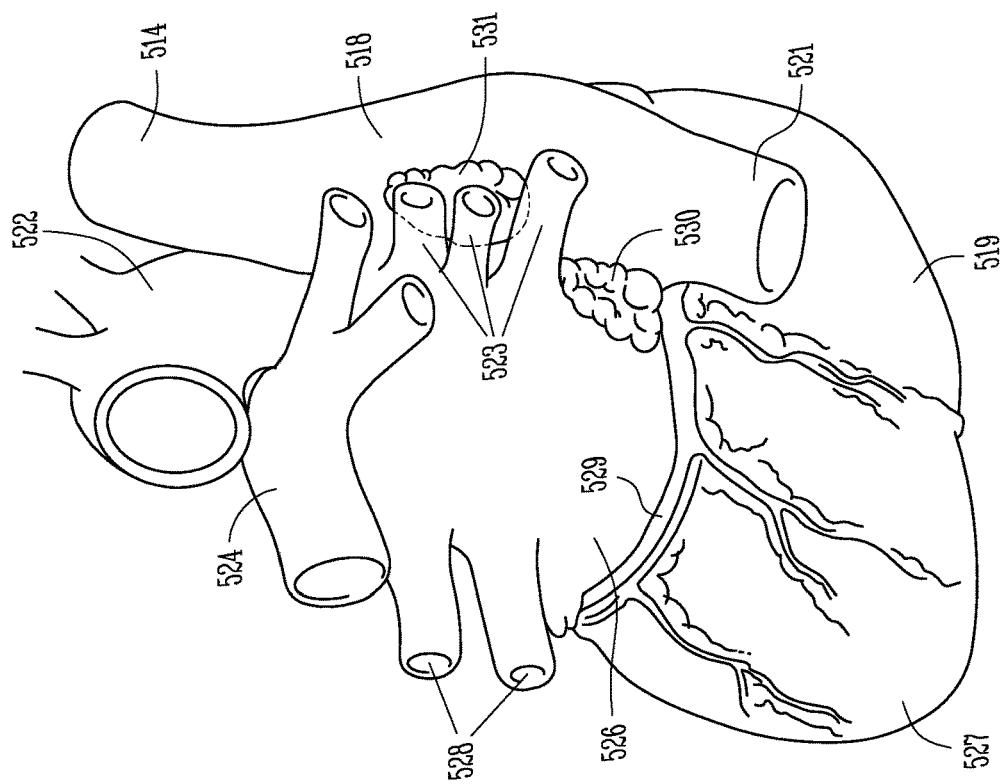
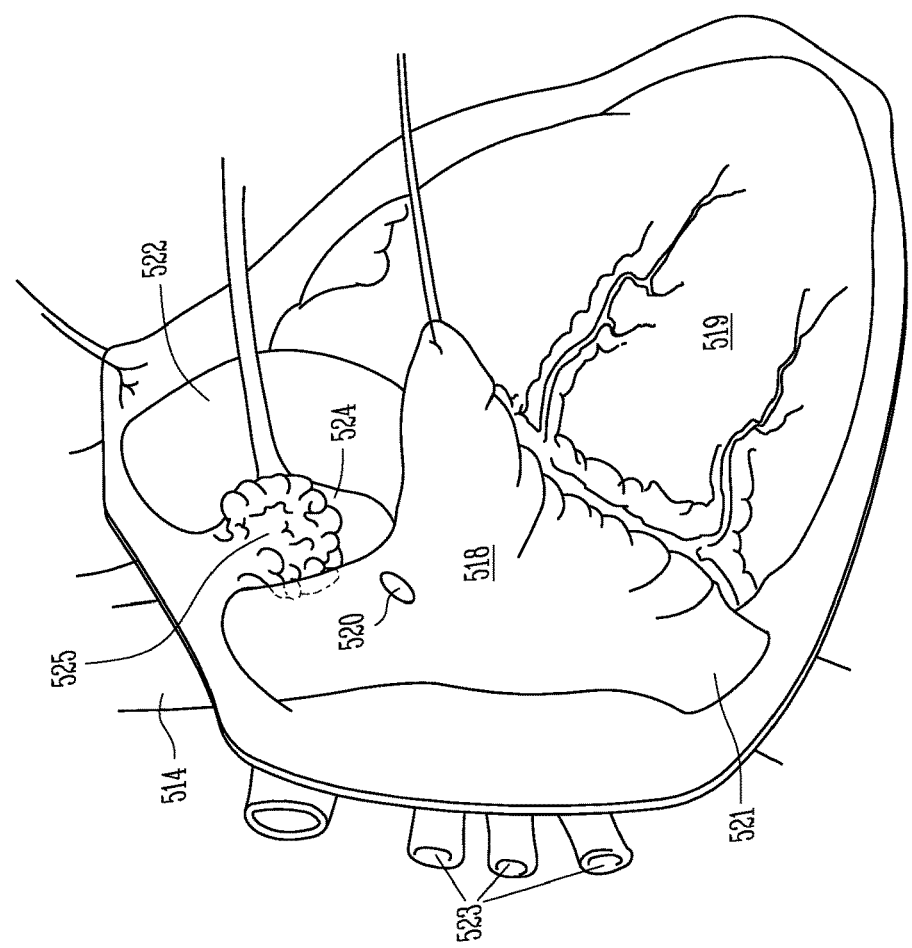
FIG. 5A
FIG. 5B

HEART FAILURE MANAGEMENT

CLAIM OF PRIORITY

This application is a continuation of and claims the benefit of priority under 35 U.S.C. § 120 to U.S. patent application Ser. No. 15/608,692, filed on May 30, 2017, which is a continuation of and claims the benefit of priority under 35 U.S.C. § 120 to U.S. patent application Ser. No. 14/644,841, filed on Mar. 11, 2015, now issued as U.S. Pat. No. 9,669,218, which is a continuation of and claims the benefit of priority under 35 U.S.C. § 120 to U.S. patent application Ser. No. 14/143,492, filed on Dec. 30, 2013, now issued as U.S. Pat. No. 8,996,107, which is a continuation of and claims the benefit of priority under 35 U.S.C. § 120 to U.S. patent application Ser. No. 13/731,691, filed on Dec. 31, 2012, now issued as U.S. Pat. No. 8,620,427, which is a continuation of and claims the benefit of priority under 35 U.S.C. § 120 to U.S. patent application Ser. No. 13/214,564, filed on Aug. 22, 2011, now issued as U.S. Pat. No. 8,346,360, which is a continuation of and claims the benefit of priority under 35 U.S.C. § 120 to U.S. patent application Ser. No. 11/382,128, filed on May 8, 2006, now issued as U.S. Pat. No. 8,005,543, each of which is hereby incorporated by reference herein in its entirety.

FIELD OF THE INVENTION

This application relates generally to medical devices and, more particularly, to systems, devices and methods for managing heart failure using neural stimulation.

BACKGROUND

Heart failure refers to a clinical syndrome in which cardiac function causes a below normal cardiac output that can fall below a level adequate to meet the metabolic demand of peripheral tissues. Heart failure may present itself as congestive heart failure (CHF) due to the accompanying venous and pulmonary congestion. Heart failure can be due to a variety of etiologies such as ischemic heart disease. Cardiac decompensation is typically marked by dyspnea (difficulty breathing), venous engorgement and edema, and each decompensation event can cause further long term deterioration of the heart function.

Heart failure patients have reduced autonomic balance, which is associated with left ventricular dysfunction and increased mortality. Modulation of the sympathetic and parasympathetic nervous systems has potential clinical benefit in preventing remodeling and death in heart failure and post-MI (myocardial infarction) patients.

Clinicians set measured parameter thresholds in some known implantable medical devices, such as pacemakers, defibrillators, cardiac resynchronization devices, and the like. The threshold for each parameter may vary from patient to patient. Appropriate device therapy is triggered when a threshold is crossed. Treatment can be initiated by non-events that include measurements above at least some thresholds. These non-events are also referred to as false positives. Therapy delivered for false positives depletes battery power and may increase the risk of overstimulating the patient.

Improved methods and systems are needed to accurately determine heart failure status, and to provide heart failure therapy using the accurately-determined heart failure status.

SUMMARY

Various aspects of the present subject matter relate to a system. Various system embodiments comprise a stimulator adapted to deliver a stimulation signal for a heart failure therapy, a number of sensors adapted to provide at least a first measurement of a heart failure status and a second measurement of the heart failure status, and a controller. The controller is connected to the stimulator and to the number of sensors. The controller is adapted to use the first and second measurements to create a heart failure status index, and control the stimulator to modulate the signal using the index.

Various aspects of the present subject matter relate to a method. According to various embodiments of the method, a first measurement of a heart failure status and a second measurement of the heart failure status are obtained. A heart failure index is created using the first measurement and the second measurement. A heart failure therapy is adjusted using the heart failure index as an indicator of the heart failure status.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

FIGS. 5A and 5B illustrate the right side and left side of the heart, respectively, and further illustrate cardiac fat pads which provide neural targets for some neural stimulation therapies.

DETAILED DESCRIPTION

Figure 1A:
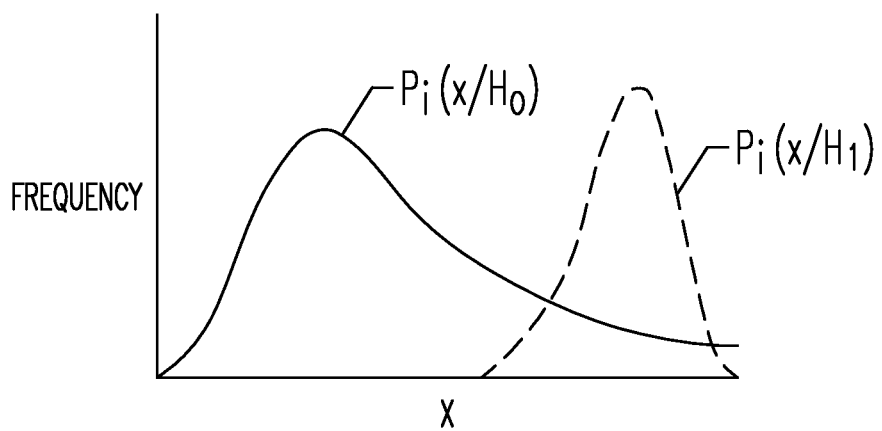
FIG. 1A shows an example of a probability density function $p_i(x|H_0)$ based upon measurements taken over a period time for a physiological parameter of a patient.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The present subject matter provides an index for heart failure (HF) status using at least two measured HF parameters. Embodiments provide a closed-loop neural stimulation system for heart failure (HF) therapy that modulates the therapy based on a heart failure status. Embodiments of the system include an implantable neural stimulator. A neurostimulation therapy is applied to prevent or slow reverse remodeling in HF patients. The HF status is determined by a combination of physiological variables derived from a suite of physiological sensors. For example, the HF status can be determined as a composite index using two or more measured parameters related to HF status. Examples of measured parameters related to HF status include heart rate variability (HRV), heart rate turbulence (HRT), heart sounds, activity, transthoracic impedance, minute ventilation, pulmonary artery pressure, and electrogram features.

Neural stimulation parameter modulation can occur in response to changes in any or all of the parameters used to create the HF status index. Some of the measured parameters that make up the index can be updated continuously within the constraints of the device(s) used to perform the measurements, while other measured parameters are updated intermittently or updated periodically (e.g. hourly, daily, etc.). Various embodiments trend the parameters to monitor changes. Indices of chronic worsening heart failure (such as lower SDANN for an HRV analysis, higher minimum heart rate, weaker RSA coupling and physiologic response to activity as will be discussed below) triggers a shift towards neural stimulation therapy to elicit a parasympathetic response (stimulating parasympathetic nerve traffic and/or inhibiting sympathetic nerve traffic), and indices of improving heart failure (reversed trend of the indices above) triggers a shift away from eliciting a parasympathetic response (e.g. reduce intensity of stimulation) or trigger a shift to elicit a sympathetic response (stimulating sympathetic nerve traffic and/or inhibiting parasympathetic nerve traffic). HRV, SDANN and RSA are discussed below. Neural stimulation parameters include amplitude, frequency, duty cycle, pulse width, and stimulation site, and any or all of these parameters can be modulated to shift autonomic balance towards greater or lesser parasympathetic response or between a parasympathetic response and a sympathetic response.

Control systems according to embodiments of the present subject matter efficiently manage battery power and reduce the risk of patient over-stimulation by reducing false positives. Embodiments of the device have a dual feedback response to account for long-term and short-term changes. Variables indicative of chronic changes in heart failure status are used to titrate the application of neural stimulation therapy (e.g. increased parasympathetic stimulation in response to worsening heart failure status). The dual feedback device embodiments also respond to variables indicative of short-term changes in HF status (e.g. an approaching decompensation event) and apply emergency neural stimulation therapy to prevent or delay the decompensation event. For example, appropriate neural stimulation can be provided to elicit an appropriate sympathetic response for a short term to maintain cardiac output until the patient can reach a clinical setting.

Various device embodiments provide cardiac rhythm management therapy, including pacing, defibrillation, and/or cardiac resynchronization therapy, and use the HF status to control these therapies. Some embodiment provide a CRM therapy in addition to a neural stimulation HF therapy. The feedback sensors can be integrated into the implantable device, or external to the body, or both. The device can wirelessly communicate with an external monitor, allowing the system to monitor, record, and trend HF status and therapy application, and to provide alerts based on changes in HF status.

The discussion that follows is organized into a brief discussion of physiology, examples of HF status parameters, a discussion of the HF status index based on at least two HF status parameters, a discussion of therapies including neural stimulation and myocardial stimulation, device embodiments and system embodiments.

Physiology

Provided below is a brief discussion of the nervous system, heart failure, hypertension and cardiac remodeling.

This discussion is believed to assist a reader in understanding the disclosed subject matter.

Nervous System

The autonomic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes, but is not limited to, the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system. Afferent nerves convey impulses toward a nerve center, and efferent nerves convey impulses away from a nerve center.

The heart rate and force is increased when the sympathetic nervous system is stimulated, and is decreased when the sympathetic nervous system is inhibited (the parasympathetic nervous system is stimulated). Cardiac rate, contractility, and excitability are known to be modulated by centrally mediated reflex pathways. Baroreceptors and chemoreceptors in the heart, great vessels, and lungs, transmit cardiac activity through vagal and sympathetic afferent fibers to the central nervous system. Activation of sympathetic afferents triggers reflex sympathetic activation, parasympathetic inhibition, vasoconstriction, and tachycardia. In contrast, parasympathetic activation results in bradycardia, vasodilation, and inhibition of vasopressin release. Among many other factors, decreased parasympathetic or vagal tone or increased sympathetic tone is associated with various arrhythmias genesis, including ventricular tachycardia and atrial fibrillation.

Baroreflex is a reflex triggered by stimulation of a baroreceptor. A baroreceptor includes any sensor of pressure changes, such as sensory nerve endings in the wall of the auricles of the heart, vena cava, aortic arch and carotid sinus, that is sensitive to stretching of the wall resulting from increased pressure from within, and that functions as the receptor of the central reflex mechanism that tends to reduce that pressure. Clusters of nerve cells can be referred to as autonomic ganglia. These nerve cells can also be electrically stimulated to induce a baroreflex, which inhibits the sympathetic nerve activity and stimulates parasympathetic nerve activity. Autonomic ganglia thus forms part of a baroreflex pathway. Afferent nerve trunks, such as the vagus, aortic and carotid nerves, leading from the sensory nerve endings also form part of a baroreflex pathway. Stimulating a baroreflex pathway and/or baroreceptors inhibits sympathetic nerve activity (stimulates the parasympathetic nervous system) and reduces systemic arterial pressure by decreasing peripheral vascular resistance and cardiac contractility. Baroreceptors are naturally stimulated by internal pressure and the stretching of vessel wall (e.g. arterial wall).

Stimulating the sympathetic and parasympathetic nervous systems can have effects other than heart rate and blood pressure. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intention, increases urine secretion, and contracts the wall and relaxes the sphincter of the bladder. The functions associated with the sympathetic and parasympathetic nervous systems are many and can be complexly integrated with each other.

Neural stimulation can be used to stimulate nerve traffic or inhibit nerve traffic. An example of neural stimulation to stimulate nerve traffic is a lower frequency signal (e.g. within a range on the order of 20 Hz to 50 Hz). An example of neural stimulation to inhibit nerve traffic is a higher frequency signal (e.g. within a range on the order of 120 Hz to 150 Hz). Other methods for stimulating and inhibiting nerve traffic has been proposed. According to various embodiments of the present subject matter, sympathetic neural targets include, but are not limited to, a peroneal nerve, a sympathetic column in a spinal cord, and cardiac post-ganglionic sympathetic neurons. According to various embodiments of the present subject matter, parasympathetic neural targets include, but are not limited to, a vagus nerve, a baroreceptor, and a cardiac fat pad.

Heart Failure

Heart failure refers to a clinical syndrome in which cardiac function causes a below normal cardiac output that can fall below a level adequate to meet the metabolic demand of peripheral tissues. Heart failure may present itself as congestive heart failure (CHF) due to the accompanying venous and pulmonary congestion. Heart failure can be due to a variety of etiologies such as ischemic heart disease. Heart failure patients have reduced autonomic balance, which is associated with LV dysfunction and increased mortality. Modulation of the sympathetic and parasympathetic nervous systems has potential clinical benefit in preventing remodeling and death in heart failure and post-MI patients. Direct electrical stimulation can activate the baroreflex, inducing a reduction of sympathetic nerve activity and reducing blood pressure by decreasing vascular resistance. Sympathetic inhibition and parasympathetic activation have been associated with reduced arrhythmia vulnerability following a myocardial infarction, presumably by increasing collateral perfusion of the acutely ischemic myocardium and decreasing myocardial damage.

Hypertension

Hypertension is a cause of heart disease and other related cardiac co-morbidities. Hypertension occurs when blood vessels constrict. As a result, the heart works harder to maintain flow at a higher blood pressure, which can contribute to heart failure. Hypertension generally relates to high blood pressure, such as a transitory or sustained elevation of systemic arterial blood pressure to a level that is likely to induce cardiovascular damage or other adverse consequences. Hypertension has been arbitrarily defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease.

A large segment of the general population, as well as a large segment of patients implanted with pacemakers or defibrillators, suffer from hypertension. The long term mortality as well as the quality of life can be improved for this population if blood pressure and hypertension can be reduced. Many patients who suffer from hypertension do not respond to treatment, such as treatments related to lifestyle changes and hypertension drugs.

Cardiac Remodeling

Following myocardial infarction (MI) or other cause of decreased cardiac output, a complex remodeling process of the ventricles occurs that involves structural, biochemical, neurohormonal, and electrophysiologic factors. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation.

As the heart begins to dilate, afferent baroreceptor and cardiopulmonary receptor signals are sent to the vasomotor central nervous system control center, which responds with hormonal secretion and sympathetic discharge. It is the combination of hemodynamic, sympathetic nervous system and hormonal alterations (such as presence or absence of angiotensin converting enzyme (ACE) activity) that ultimately account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction (decompensation). It has been shown that the extent of ventricular remodeling is positively correlated with increased mortality in post-MI and heart failure patients.

HF Status Parameters

Examples of parameters that can be used to determine a HF status include heart rate variability (HRV), heart rate turbulence (HRT), heart sounds, electrogram features, activity, respiration, and pulmonary artery pressure. These parameters are briefly discussed below.

Respiration parameters, for example, can be derived from a minute ventilation signal and a fluid index can be derived from transthoracic impedance. For example decreasing thoracic impedance reflects increased fluid buildup in lungs, and indicates a progression of heart failure. Respiration can significantly vary a minute ventilation. The transthoracic impedance can be totaled or averaged to provide a indication of fluid buildup.

HRV

Heart Rate Variability (HRV) is one technique that has been proposed to assess autonomic balance. HRV relates to the regulation of the sinoatrial node, the natural pacemaker of the heart by the sympathetic and parasympathetic branches of the autonomic nervous system. An HRV assessment is based on the assumption that the beat-to-beat fluctuations in the rhythm of the heart provide us with an indirect measure of heart health, as defined by the degree of balance in sympathetic and vagus nerve activity.

The time interval between intrinsic ventricular heart contractions changes in response to the body's metabolic need for a change in heart rate and the amount of blood pumped through the circulatory system. For example, during a period of exercise or other activity, a person's intrinsic heart rate will generally increase over a time period of several or many heartbeats. However, even on a beat-to-beat basis, that is, from one heart beat to the next, and without exercise, the time interval between intrinsic heart contractions varies in a normal person. These beat-to-beat variations in intrinsic heart rate are the result of proper regulation by the autonomic nervous system of blood pressure and cardiac output; the absence of such variations indicates a possible deficiency in the regulation being provided by the autonomic nervous system. One method for analyzing HRV involves detecting intrinsic ventricular contractions, and recording the time intervals between these contractions, referred to as the R-R intervals, after filtering out any ectopic contractions (ventricular contractions that are not the result of a normal sinus rhythm). This signal of R-R intervals is typically transformed into the frequency-domain, such as by using fast Fourier transform ("FFT") techniques, so that its spectral frequency components can be analyzed and divided into low and high frequency bands. For example, the low frequency (LF) band can correspond to a frequency ("f") range $0.04$ Hz$\leq$f$<0.15$ Hz, and the high frequency (HF) band can correspond to a frequency range $0.15$ Hz$\leq$f$\leq 0.40$ Hz. The HF band of the R-R interval signal is influenced only by the parasympathetic/vagal component of the autonomic nervous system. The LF band of the R-R interval signal is influenced by both the sympathetic and parasympathetic components of the autonomic nervous system. Consequently, the ratio LF/HF is regarded as a good indication of the autonomic balance between sympathetic and parasympathetic/vagal components of the autonomic nervous system. An increase in the LF/HF ratio indicates an increased predominance of the sympathetic component, and a decrease in the LF/HF ratio indicates an increased predominance of the parasympathetic component. For a particular heart rate, the LF/HF ratio is regarded as an indication of patient wellness, with a lower LF/HF ratio indicating a more positive state of cardiovascular health. A spectral analysis of the frequency components of the R-R interval signal can be performed using a FFT (or other parametric transformation, such as autoregression) technique from the time domain into the frequency domain. Such calculations require significant amounts of data storage and processing capabilities. Additionally, such transformation calculations increase power consumption, and shorten the time during which the implanted battery-powered device can be used before its replacement is required.

One example of an HRV parameter is SDANN (standard deviation of averaged NN intervals), which represents the standard deviation of the means of all the successive 5 minutes segments contained in a whole recording. Other HRV parameters can be used.

HRT

Heart rate turbulence (HRT) is the physiological response of the sinus node to a premature ventricular contraction (PVC), consisting of a short initial heart rate acceleration followed by a heart rate deceleration. HRT has been shown to be an index of autonomic function, closely correlated to HRV. HRT is believed to be an autonomic baroreflex. The PVC causes a brief disturbance of the arterial blood pressure (low amplitude of the premature beat, high amplitude of the ensuing normal beat). This fleeting change is registered immediately with an instantaneous response in the form of HRT if the autonomic system is healthy, but is either weakened or missing if the autonomic system is impaired.

By way of example and not limitation, it has been proposed to quantify HRT using Turbulence Onset (TO) and Turbulence Slope (TS). TO refers to the difference between the heart rate immediately before and after a PVC, and can be expressed as a percentage. For example, if two beats are evaluated before and after the PVC, TO can be expressed as:

$$TO\ \% = \frac{(RR_{+1} + RR_{+2}) - (RR_{-2} + RR_{-1})}{(RR_{-2} + RR_{-1})} * 100.$$

$RR_{-2}$ and $RR_{-1}$ are the first two normal intervals preceding the PVC and $RR_{+1}$ and $RR_{-2}$ are the first two normal intervals following the PVC. In various embodiments, TO is determined for each individual PVC, and then the average value of all individual measurements is determined. However, TO does not have to be averaged over many measurements, but can be based on one PVC event. Positive TO values indicate deceleration of the sinus rhythm, and negative values indicate acceleration of the sinus rhythm. The number of R-R intervals analyzed before and after the PVC can be adjusted according to a desired application. TS, for example, can be calculated as the steepest slope of linear regression for each sequence of five R-R intervals. In various embodiments, the TS calculations are based on the averaged tachogram and expressed in milliseconds per RR interval. However, TS can be determined without averaging. The number of R-R intervals in a sequence used to determine a linear regression in the TS calculation also can be adjusted according to a desired application.

Rules or criteria can be provided for use to select PVCs and for use in selecting valid RR intervals before and after the PVCs. A PVC event can be defined by an R-R interval in some interval range that is shorter than a previous interval by some time or percentage, or it can be defined by an R-R interval without an intervening P-wave (atrial event) if the atrial events are measured. Various embodiments select PVCs only if the contraction occurs at a certain range from the preceding contraction and if the contraction occurs within a certain range from a subsequent contraction. For example, various embodiments limit the HRT calculations to PVCs with a minimum prematurity of 20% and a post-extrasystole interval which is at least 20% longer than the normal interval. Additionally, pre-PVC R-R and post-PVC R-R intervals are considered to be valid if they satisfy the condition that none of the beats are PVCs. One HRT process, for example, excludes RR intervals that are less than a first time duration, that are longer than a second time duration, that differ from a preceding interval by more than a third time duration, or that differ from a reference interval by a predetermined amount time duration or percentage. In an embodiment of such an HRT process with specific values, RR intervals are excluded if they are less than 300 ms, are more than 2000 ms, differ from a preceding interval by more than 200 ms, or differ by more than 20% from the mean of the last five sinus intervals. Various embodiments of the present subject matter provide programmable parameters, such as any of the parameters identified above, for use in selecting PVCs and for use in selecting valid RR intervals before and after the PVCs.

The neural stimulation device that incorporates this technique for assessing autonomic balance can be used to provide either parasympathetic stimulation or inhibition or sympathetic stimulation or inhibition. Various device embodiments include means for pacing a ventricle, such as at least one ventricular pacing lead. To measure autonomic balance for closed-loop therapy titration, the device intermittently introduces or senses a PVC, and measures the resulting heart rate turbulence, as described above.

Benefits of using HRT to monitor autonomic balance include the ability to measure autonomic balance at a single moment in time. Additionally, unlike the measurement of HRV, HRT assessment can be performed in patients with frequent atrial pacing. Further, HRT analysis provides for a simple, non-processor-intensive measurement of autonomic balance. Thus, data processing, data storage, and data flow are relatively small, resulting in a device with less cost and less power consumption. Also, HRT assessment is faster than HRV, requiring much less R-R data. HRT allows assessment over short recording periods similar in duration to typical neural stimulation burst durations, such as on the order of tens of seconds, for example.

Heart Sounds

Distinguishable heart sounds include the following four heart sounds. The first heart sound ($S_1$), is initiated at the onset of ventricular systole and consists of a series of vibrations of mixed, unrelated, low frequencies. It is the loudest and longest of the heart sounds, has a decrescendo quality, and is heard best over the apical region of the heart. The tricuspid valve sounds are heard best in the fifth intercostal space, just to the left of the sternum, and the mitral sounds are heard best in the fifth intercostal space at the cardiac apex. $S_1$ is chiefly caused by oscillation of blood in the ventricular chambers and vibration of the chamber walls. The vibrations are engendered by the abrupt rise of ventricular pressure with acceleration of blood back toward the atria, and the sudden tension and recoil of the A-V valves and adjacent structures with deceleration of the blood by the closed A-V valves. The vibrations of the ventricles and the contained blood are transmitted through surrounding tissue and reach the chest wall where they may be heard or recorded. The intensity of $S_1$ is primarily a function of the force of the ventricular contraction, but also of the interval between atrial and ventricular systoles. If the A-V valve leaflets are not closed prior to ventricular systole, greater velocity is imparted to the blood moving toward the atria by the time the A-V valves are snapped shut by the rising ventricular pressure, and stronger vibrations result from this abrupt deceleration of the blood by the closed A-V valves.

The second heart sound ($S_2$), which occurs on closure of the semi-lunar valves, is composed of higher frequency vibrations, is of shorter duration and lower intensity, and has a more "snapping" quality than the first heart sound. The second sound is caused by abrupt closure of the semi-lunar valves, which initiates oscillations of the columns of blood and the tensed vessel walls by the stretch and recoil of the closed valve. Conditions that bring about a more rapid closure of the semi-lunar valve, such as increases in pulmonary artery or aorta pressure (e.g., pulmonary or systemic hypertension), will increase the intensity of the second heart sound. In the adult, the aortic valve sound is usually louder than the pulmonic, but in cases of pulmonary hypertension, the reverse is often true.

The third heart sound ($S_3$), which is more frequently heard in children with thin chest walls or in patients with rapid filling wave due to left ventricular failure, consists of a few low intensity, low-frequency vibrations. It occurs in early diastole and is believed to be due to vibrations of the ventricular walls caused by abrupt acceleration and deceleration of blood entering the ventricles on opening of the atrial ventricular valves. A fourth or atrial sound ($S_4$), consisting of a few low-frequency oscillations, is occasionally heard in normal individuals. It is caused by oscillation of blood and cardiac chambers created by atrial contraction. Accentuated $S_3$ and $S_4$ sounds may be indicative of certain abnormal conditions and are of diagnostic significance.

Thus, a heart sound can be used in determining a heart failure status. For example, a more severe HF status tends to be reflected in a larger $S_3$ amplitude.

Electrograms

Example of ECG features that can be extracted to provide an indicator of HF status include a QRS complex duration due to left bundle branch block, ST segment deviation, and a Q wave due to myocardial infarction. Any one or combination of these features can be used to provide the indicator of HF status. Other features can be extracted from the ECG.

Activity

Activity sensors can be used to assess the activity of the patient. Sympathetic activity naturally increases in an active patient, and decreases in an inactive patient. Thus, activity sensors can provide a contextual measurement for use in determining the autonomic balance of the patient, and thus the HF status of the patient. Various embodiments, for example, provide a combination of sensors to trend heart rate and/or respiration rate to provide an indicator of activity.

Respiration

Two methods for detecting respiration involve measuring a transthoracic impedance and minute ventilation. Respiration can be an indicator of activity, and can provide an explanation of increased sympathetic tone that does not directly related to a HF status. For example, it may not be appropriate to change a HF therapy due to a detected increase in sympathetic activity attributable to exercise.

Respiration measurements (e.g. transthoracic impedance) can also be used to measure Respiratory Sinus Arrhythmia (RSA). RSA is the natural cycle of arrhythmia that occurs through the influence of breathing on the flow of sympathetic and vagus impulses to the sinoatrial node. The rhythm of the heart is primarily under the control of the vagus nerve, which inhibits heart rate and the force of contraction. The vagus nerve activity is impeded and heart rate begins to increase when a breath is inhaled. When exhaled, vagus nerve activity increases and the heart rate begins to decrease. The degree of fluctuation in heart rate is also controlled significantly by regular impulses from the baroreceptors (pressure sensors) in the aorta and carotid arteries. Thus, a measurement of autonomic balance can be provided by correlating heart rate to the respiration cycle.

Pulmonary Artery Pressure

As identified above, high blood pressure can contribute to heart failure. Chronically high blood pressure, or a chronic blood pressure that trends higher, provides an indication of an increased likelihood of heart failure. Various embodiments use pulmonary artery pressure to approximate filling pressure. Filling pressure is a marker of preload, and preload is an indicator of heart failure status.

HF Status Index

Embodiments of the present subject matter provide a HF status index using two or more HF parameters, such as any two or more of the HF parameters identified above. The index reduces the false positives, and thus reduces power drain associated with unneeded therapy and also reduces the risk of overstimulation for the patient. Embodiments of the index include a composite index, where each HF parameters used as an input is appropriately weighted to generated the composite index. For example, index can be provided by (parameter 1)*A+(parameter 2)*B. In another example, index includes a product of the parameters (e.g. (parameter 1)*(parameter 2)), or can include on parameter divided by another (e.g. (parameter 1)/(parameter 2)). Other algorithms can be used to create an index from the two or more parameters.

Other examples of creating an index based on two or more HF-related parameters to control a therapy are provided below. These examples include the use of statistical probabilities and the use of an intelligent system to determine a HF status based on two or more HF parameters.

Statistical Probabilities

U.S. application Ser. No. 11/276,735, filed Mar. 13, 2006, issued as U.S. Pat. No. 7,713,213, and entitled "Physiological Event Detection Systems and Methods," which is incorporated by reference, discusses the problems of false positives using probability densities. FIG. 1A shows an example of a probability density function $p_i(x|H_0)$ based upon measurements taken over a period time for a physiological parameter (e.g., heart sound amplitude, heart rate and the like) of a patient. The illustrated function $p_i(x|H_0)$ shows a distribution for non-event (baseline) measurements taken for the physiological parameter, and thus represents a distribution of measurements for a stable patient. These measurements statistically characterize the non-event environment of the patient (i.e., no heart failure, arrhythmia, and the like). The probability density function $p_i(x|H_1)$ shown in dashed lines in FIG. 1A, illustrates an estimated distribution of measurements for a physiological parameter representative of an "event" condition (e.g., heart failure and the like). Because event measurements are typically rare, the function $p_i(x|H_1)$ typically only approximates the distribution of event-related measurements. $H_1$ thereby is the hypothesis showing events of significance. In another example, $H_1$ is estimated from a population of past events. As shown in FIG. 1A and further described below, outlier measurements of the physiological parameter that approach the event distribution $p_i(x|H_1)$ are less likely to be a false alarm (i.e., decreased probability of not being indicative of an event), and conversely an increased probability of being indicative of an event (e.g., heart failure, arrhythmia and the like). Conceptually, measurements that are outliers for $p_i(x|H_0)$ more closely resemble event measurements than non-event measurements.

In various embodiments, the probability density function $p_i(x|H_0)$ is generated using a histogram of actual measured values. The actual measured values are used to directly estimate the probability density function. Properties of the measurements (e.g., median and percentile measure) are used to create the probability density function. In various embodiments, a particular probability distribution is used, such as a Gaussian distribution or other function that is specified mathematically (e.g., by estimating the mean and standard deviation) or otherwise. In various embodiments, the probability density function is generated by curve-fitting over histogram data. The measurements used to generate the probability density function $p_i(x|H_0)$ are collected and stored.

In certain examples, particular measurements are excluded from use in computing the probability density function $p(x_i|H_0)$, such as corrupted measurements, old measurements, event-related measurements—the function $p_i(x|H_0)$ should only include non-event data—and the like. In one example, the probability distribution function is generated with measurements taken during a particular (e.g., moving) window of time. In certain examples, the moving window of time extends a specified interval back from the time of the most recent measurement of the physiological parameter. In certain examples, older measurements outside of the moving window of time are excluded from use in computing the probability distribution function. This allows the probability distribution function to update and follow gradual drifts in the physiological parameter by using the most recent measurements. Older measurements can be stored in the implantable medical device and/or external system, such as for historical use. Additionally, where measurements are determined to indicate an event, as described below, such event-related measurements are flagged and excluded from use in generating the non-event probability distribution function.

In certain examples, measurements that are deemed unreliable or corrupted are not used to compute the non-event probability distribution function. For example, certain physiological parameters are confounded by other effects. For example, heart sounds may be affected by posture. A second sensor (e.g., a posture detector) can be used to detect posture to "qualify" the heart sounds data, such that only heart sounds associated with a particular posture are used to compute a particular probability distribution function—or different probability distribution functions can be computed for various postures. Similarly, certain physiological parameters are affected by sleep state, such that measurements generated during periods of rest, such as sleep, may vary from measurements taken during waking hours. In this example, a sleep detector may be used to qualify the primary physiological parameter according to a particular sleep state. Activity can also affect sensed physiological parameters. In general, one or more secondary physiological sensors can be used to qualify data from a primary physiological sensor to remove unreliable or corrupted data from use in computing the probability distribution function, which is also useful in a situation in which the primary physiological sensor fails. Thus, according to the present subject matter, two or more sensors can be used to create an index for a HF status, such as may be presented by the non-event probability distribution function.

Figure 1B:
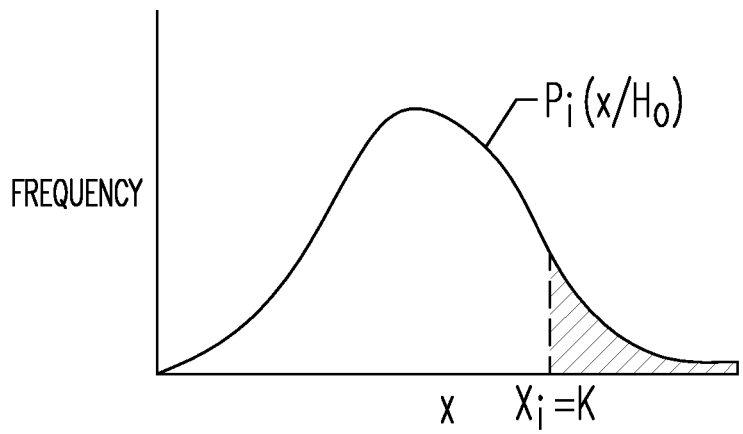
FIG. 1B shows one example of the non-event probability density function $p(x_i|H_0)$.

FIG. 1B shows one example of the non-event probability density function $p_i(x|H_0)$. As described above, the function $p_i(x|H_0)$ is typically derived from non-event measurements taken by a sensor of a physiological parameter for the patient. A measurement, such as an instant measurement $x_i=k$ can be plotted along the probability density function $p_i(x|H_0)$ and a confidence is derived by integrating the tail area based on the following equation:

$$C_i = \int_k^\infty p_i(x|H_0)dx$$

The confidence $C_i$ is proportional to the instantaneous probability the measurement k is a false alarm (i.e., a non-event measurement). Integration of the probability density function $p_i(x|H_0)$ tail area from the measurement k toward the end of the distribution thereby determines the instantaneous probability that k is a false alarm. A measurement that approaches the end of the distribution has a decreased probability that it indicates a false alarm. It is conversely more probable that such a measurement is indicative of an event, such as the onset of an abnormal condition (e.g., heart failure). The measurement k is typically an existing measurement already recorded.

Figure 1C:
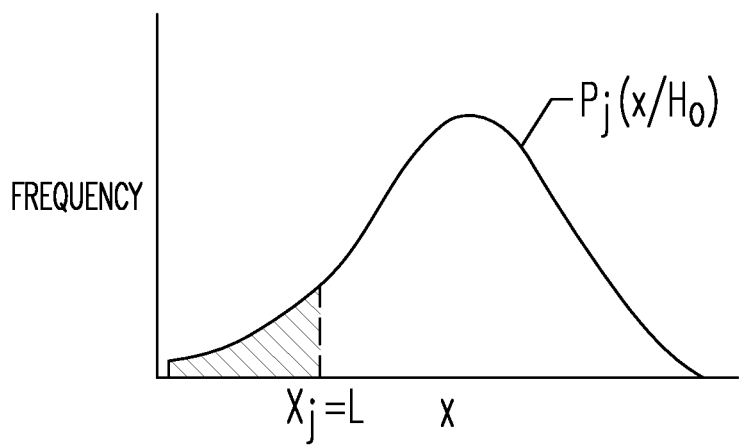
FIG. 1C shows another example, in which a function $p_j(x|H_0)$ is represented by a negative-tailed distribution of measurements for a physiological parameter, such as may be used to determine when to deliver HF therapy, according to various embodiments.

FIG. 1C shows another example, in which a function $p_j(x|H_0)$ is represented by a negative-tailed distribution of measurements for a physiological parameter. One example of a physiological parameter having a negative-tailed distribution is near-DC thoracic impedance. Generally, depressed DC thoracic impedance measurements (e.g., intrathoracic total impedance) indicate fluid accumulation, which may be associated with pulmonary edema. Therefore, such depressed DC thoracic impedance measurements represent a decreased probability of false alarm in a pulmonary edema detection scheme. Like the function $p_i(x|H_0)$, function $p_j(x|H_0)$ is typically derived from non-event measurements taken by a sensor of a physiological parameter for the patient. A measurement, such as an instant measurement $x_j=1$ can be plotted along the probability density function $p_j(x|H_0)$ and a confidence is derived by integrating the tail area based on the following equation:

$$C_j = \int_{-\infty}^l p_j(x|H_0)dx$$

The confidence $C_j$ is proportional to the instantaneous probability the measurement 1 is a false alarm (i.e., a non-event measurement). Integration of the probability density function $p_j(x|H_0)$ tail area from the measurement 1 toward the left end of the distribution determines the instantaneous probability that 1 is a false alarm. As with the function $p_i(x|H_0)$, a measurement that approaches the end of the distribution, has a decreased instantaneous probability that it indicates a false alarm, and it is conversely more probable that the measurement is indicative of an event, such as the onset of a condition (e.g., heart failure). Optionally, the value corresponding to the "end" of the distribution need not occur+/−infinity, but can instead be approximated using the estimated end of the distribution (e.g., an approximated value approaching a measured end of the distribution, an actual measured value, a value approaching+/−infinity and the like).

In certain examples, the clinician sets a threshold based on a constant specified false alarm rate (FAR) (i.e., constant false alarm rate). For example, the physician can specify that the threshold should be automatically set such that it yields false alarms approximately 5% (0.05) of the time. This specified FAR is independent of any statistical-based analysis of the distribution for a physiological parameter and thereby independent of any influence from the distribution. From the clinician-specified FAR, a threshold can be automatically determined, such as to compare against the values corresponding to the confidences generated with equations, such as those shown for $C_i$ and $C_j$. If the values corresponding to the confidences exceed the FAR-based threshold, then, in certain examples, a therapy is provided in response to the detected physiological event. In one example, the threshold is a value proportional to a specificity desired by the clinician. For instance, in a situation where the patient is susceptible to a condition (e.g., has shown precursor symptoms, has a history of condition and the like) the clinician would likely set a low threshold to ensure that a patient at higher risk of the condition is provided therapy. In another example, where the patient is unlikely to experience the condition (e.g., the patient has a combination pacemaker/defibrillator, but is not expected to experience heart failure) the clinician would set a high threshold to ensure that the low risk patient is only treated if measurements indicate there is a high instantaneous probability of the onset of the condition.

Intelligent System

U.S. Published Patent Application 20060010090, incorporated by reference herein, provides an example of an intelligent system that provides remote monitoring of patients in an ambulatory setting using data from a combination of implantable and external sensors. In various embodiments, a variety of sensor signals are continuously monitored and the data is collected in real time. The data, in one example, is processed by the intelligent system and upon certain conditions, a therapy is titrated and/or an alert notification is sent to a physician or a patient.

A combination of sensors provide chronic patient data under various conditions and measured in various manners. For example, a combination of sensor data is used to detect the patient's hemodynamic state and facilitate assessment of congestion, perfusion, contractility or various other conditions. In various embodiments, heart failure or other conditions are assessed.

In one example, the system includes an inference engine which assembles the information coming from different sources and provides a concise summary of heart failure, also referred to herein as a heart failure index. The different sources, in various examples, includes implantable sensors as well as external sensors.

Figure 2:
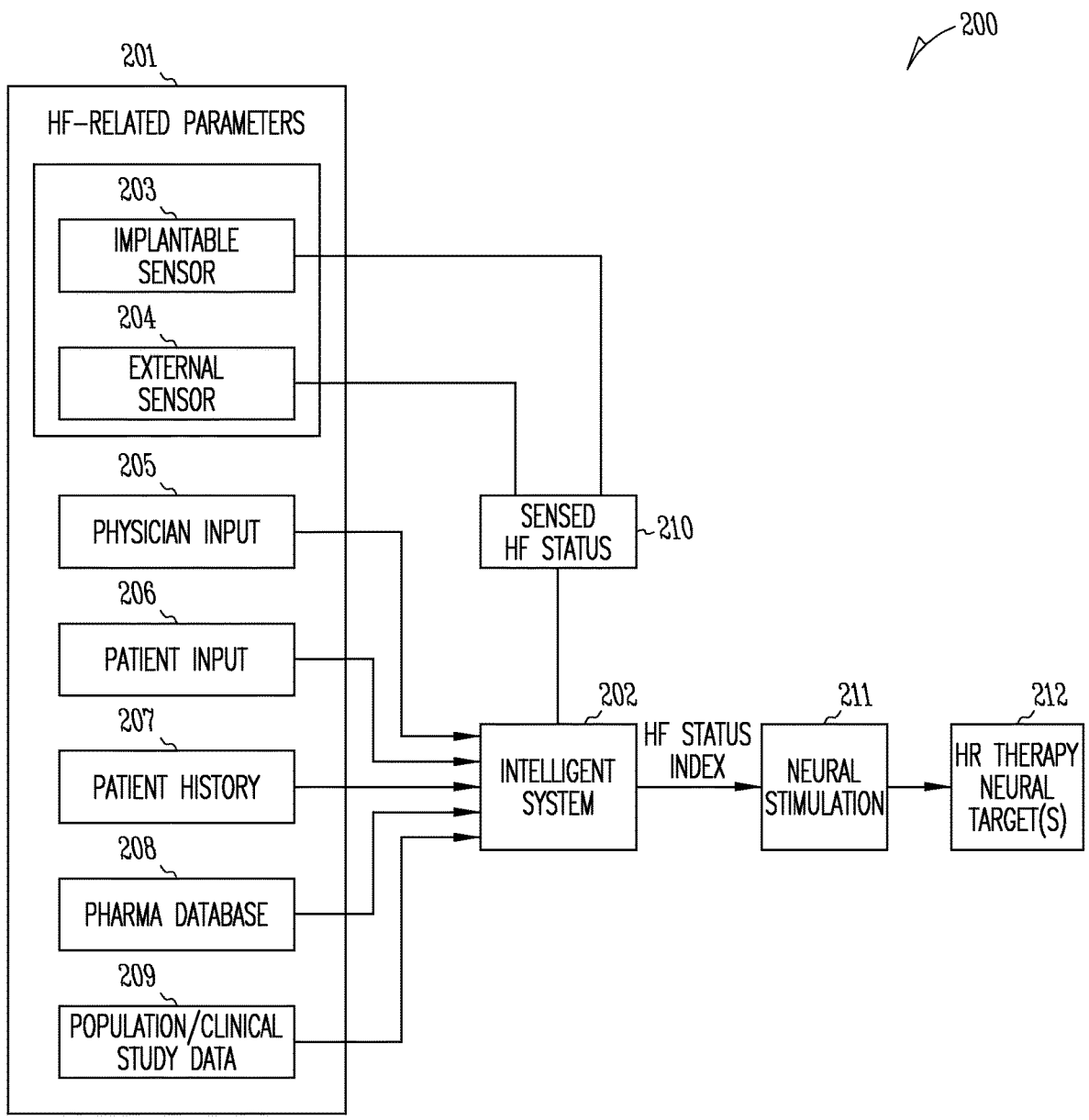
FIG. 2 illustrates system having a plurality of data sources of parameters related to heart failure coupled to an intelligent system, such as may be used to determine when to deliver HF therapy, according to various embodiments.

FIG. 2 illustrates system 200 having a plurality of data sources 201 of parameters related to heart failure coupled to an intelligent system 202. The data sources 201 include but are not limited to, for example, input devices such as implantable sensor 203, external sensor 204, physician input 205, patient input 206, patient history 207, pharmaceutical database 208 and population/clinical study data 209.

The implantable sensor 203, in various embodiments, includes one or more implantable sensors, such as a transthoracic impedance sensor, a minute ventilation sensor, a respiratory rate sensor, a heart monitor, an accelerometer, an intracardiac pressure sensor, sensors for measuring HRV, sensors for measuring HRT, and other types of sensors.

The external sensor 204 includes one or more external, or non-implantable sensors, examples of which include a weighing scale (mass sensor), a blood pressure cuff (or pressure sensor), an external monitor as well as other types of ambulatory sensors. In one example, external sensor 204 includes a weighing scale which may include a digital communication link with the intelligent system 202 or which may provide data that is manually entered into a personal digital assistant (PDA) or otherwise provided to the intelligent system 202.

The physician input 205 includes an interface or data entry device accessible to a physician, medical personal or other user. Data entered by the physician includes, for example, prescription information, medical records, patient symptoms, observation data as well as other information. In one example, the physician input can be used to specify a particular value or threshold of a parameter. The physician input, in one example, allows entry of physician-established rules for performance of the system.

The patient input 206 includes an interface or data entry device accessible to a patient, a proxy for the patient or other user. Using patient input, a user is able to enter data corresponding to real time or earlier observations. In one example, the patient input allows the patient to enter data such as food intake, exercise activity, perceived sensations and symptoms and other noted phenomena.

The patient history 207 includes an interface configured to receive information including, for example, electronic medical records (EMR), clinical information system (CIS) data, or other data corresponding to a particular patient. The data can include family medical history, patient vital signs, trends and other historical medical and clinical data.

The pharmaceutical database 208 includes data correlating specific drugs with medical conditions and symptoms. In various embodiments, the pharmaceutical database includes data generated based on research corresponding to specific geographical regions of the world, including, for example, the United States. The pharmaceutical database also includes data indicating population pharmaco-kinetics for different drugs. Data included, for example, correlates the effects of a drug as a function of time after having taken the drug. In various embodiments, the pharmaceutical database includes data about the drug therapy for a particular patient.

The population/clinical study data 209 includes data indicating relationships between selected drugs, for example. In one example, the population/clinical study data includes normative and statistical data showing relationships between populations and particular drugs. In one example, the population/clinical study data includes data derived from clinical studies data for a particular population.

The intelligent system 202 includes an inference engine and is implemented, in various examples, in hardware or software. In one example, the intelligent system includes a processor executing an expert system algorithm stored in a memory. The intelligent system is configured to generate an inference based on the knowledge base and the measured input signals. Examples of inference engines include a causal probabilistic network such as a Bayesian network, fuzzy logic, a decision tree, a neural network or a self-organized map. In various embodiments, the intelligent system 202 operates on the basis of measured inputs and generates a knowledge base over a period of time.

A Bayesian network includes a conditional probability-based network that relies on Bayes theorem to characterize likelihood of different outcomes based on known prior probabilities (i.e. observed prevalence of a disease) and newly acquired information (i.e. sensor signals). Bayesian networks use causal knowledge and explicitly model probabilistic dependence and independence relationships between different events.

Fuzzy logic provides a mechanism for manipulating uncertain information and variables that do not otherwise permit simple categorization as affirmative or negative. Fuzzy logic describes the application of if-then rules to uncertain information and provides probability of outcomes based on preceding events or conditions. Fuzzy logic relies on probabilistic if-then rules. According to principles of fuzzy logic, the probability that a premise will be true is predictable, and the conclusion that follows will also occur with some probability.

A decision tree provides a method for representing multiple temporal and logical inputs and the possible outcomes based on a combination of those inputs. A decision tree does not entail probabilities associated with branches.

A neural network is a black-box information-processing device having a number of non-linear processing modules connected together by elements that have information storage and programming functions. A self-organized map is a particular type sheet-like neural network array configured to execute an adaptive algorithm capable of learning. The neural network is based on the competitive and unsupervised learning process. Other types of expert systems are also contemplated.

One ore more of the sensors 203 and 204 are used to provide a sensed HF status 210. The intelligent system 202 generates an inference (e.g. HF status index) based on a combination of information received from data sources 201. The HF status index is used to control the neural stimulation 211 to the HF therapy neural targets 212. The information derived from the data sources 201 is subject to errors and other sources of imprecision. In one example, the information is expressed using probabilities to quantify the uncertainty. For example, data derived from a clinical study might indicate that if a particular level of a parameter is noted, then with a specified level of confidence, the patient is suffering from a particular malady. Data from additional sources will further modify the confidence level of the particular conclusion and further enhance the precision of an identification. In one example, the intelligent system incorporates temporal reasoning for events that have a time lag. For example, information about an event includes a temporal stamp and the time intervals between dependent events is propagated through the network and is marked as a possible cause of a later event.

Therapies

Neural Stimulation Therapies

Examples of neural stimulation therapies include neural stimulation therapies for heart failure, for blood pressure control such as to treat hypertension, for respiratory problems such a sleep disordered breathing, for cardiac rhythm management, for myocardial infarction and ischemia, for epilepsy, for depression, for pain, for migraines, for eating disorders and obesity, and for movement disorders. This listing of other neural stimulation therapies is not intended to be an exhaustive listing.

Figure 3A:
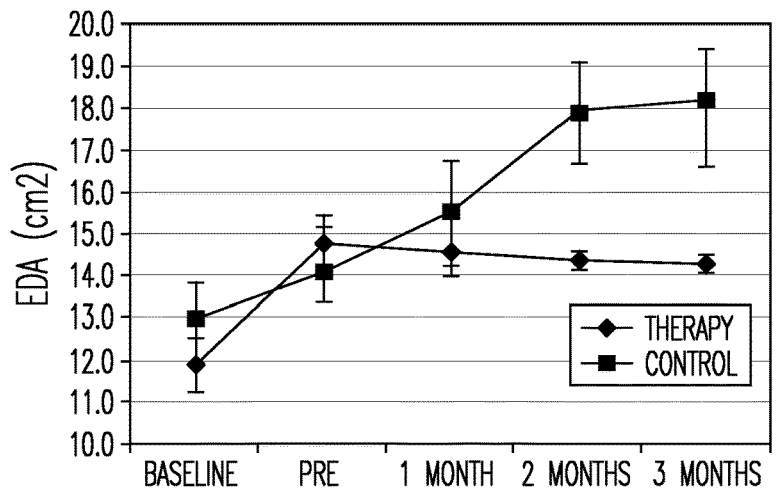
FIGS. 3A-3C illustrate the effectiveness of neural stimulation as a HF therapy.
Figure 3B:
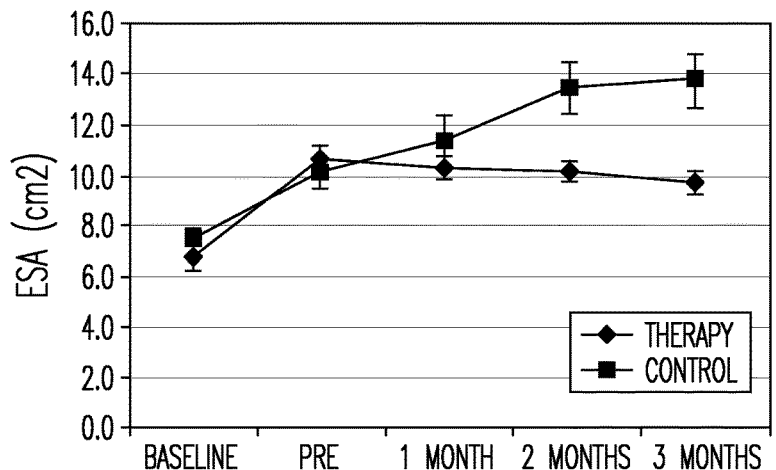
Figure 3C:
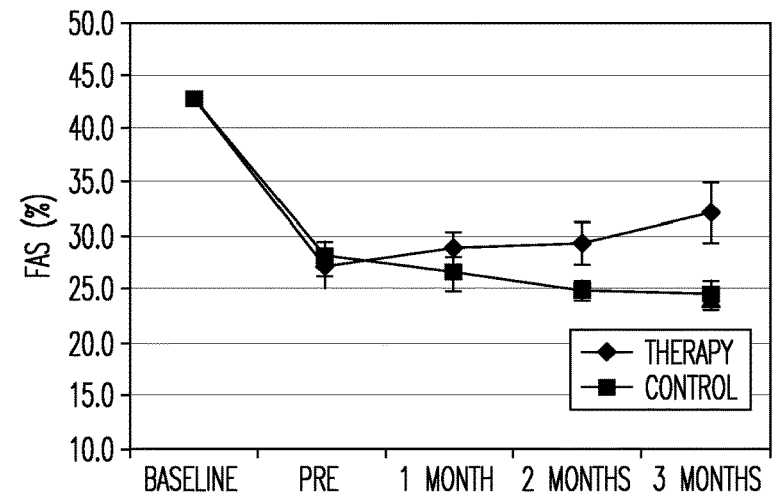

FIGS. 3A-3C illustrate that neural stimulation is effective as a HF therapy. As reflected in FIGS. 3A and 3B, neural stimulation reduces or prevents an increase in the end diastolic area and the end systolic area compared to a control group, and appears to reduce the end diastolic area and end systolic area. As reflected in FIG. 3C, neural stimulation corresponds to higher fractional shortening compared to a control group. Fractional shortening (FS) is a measure of left ventricular function, and can be calculated as:

$$FS = \frac{EDD - ESD}{EDD} * 100\%,$$

where EDD is the LV End Diastolic Dimension and ESD is the LV End Systolic Dimension.

Ventricular Remodeling

One therapy involves preventing and/or treating ventricular remodeling. Activity of the autonomic nervous system is at least partly responsible for the ventricular remodeling which occurs as a consequence of an MI or due to heart failure. It has been demonstrated that remodeling can be affected by pharmacological intervention with the use of, for example, ACE inhibitors and beta-blockers. Pharmacological treatment carries with it the risk of side effects, however, and it is also difficult to modulate the effects of drugs in a precise manner. Another issue with drug therapy is patient non-compliance. Embodiments of the present subject matter employ electrostimulatory means to modulate autonomic activity, referred to as anti-remodeling therapy or ART. When delivered in conjunction with ventricular resynchronization pacing, also referred to as remodeling control therapy (RCT), such modulation of autonomic activity acts synergistically to reverse or prevent cardiac remodeling.

Increased sympathetic nervous system activity following ischemia often results in increased exposure of the myocardium to epinephrine and norepinephrine. These catecholamines activate intracellular pathways within the myocytes, which lead to myocardial death and fibrosis. Stimulation of the parasympathetic nerves (vagus) inhibits this effect. According to various embodiments, the present subject matter selectively activates the vagal cardiac nerves in addition to CRT in heart failure patients to protect the myocardium from further remodeling and arrhythmogenesis. Other potential benefits of stimulating vagal cardiac nerves in addition to CRT include reducing inflammatory response following myocardial infarction, and reducing the electrical stimulation threshold for defibrillating. For example, when a ventricular tachycardia is sensed, vagal nerve stimulation is applied, and then a defibrillation shock is applied. The vagal nerve stimulation allows the defibrillation shock to be applied at less energy. Also, parasympathetic stimulation may terminate an arrhythmia or otherwise increase the effectiveness of an anti-arrhythmia treatment.

Figure 4A:
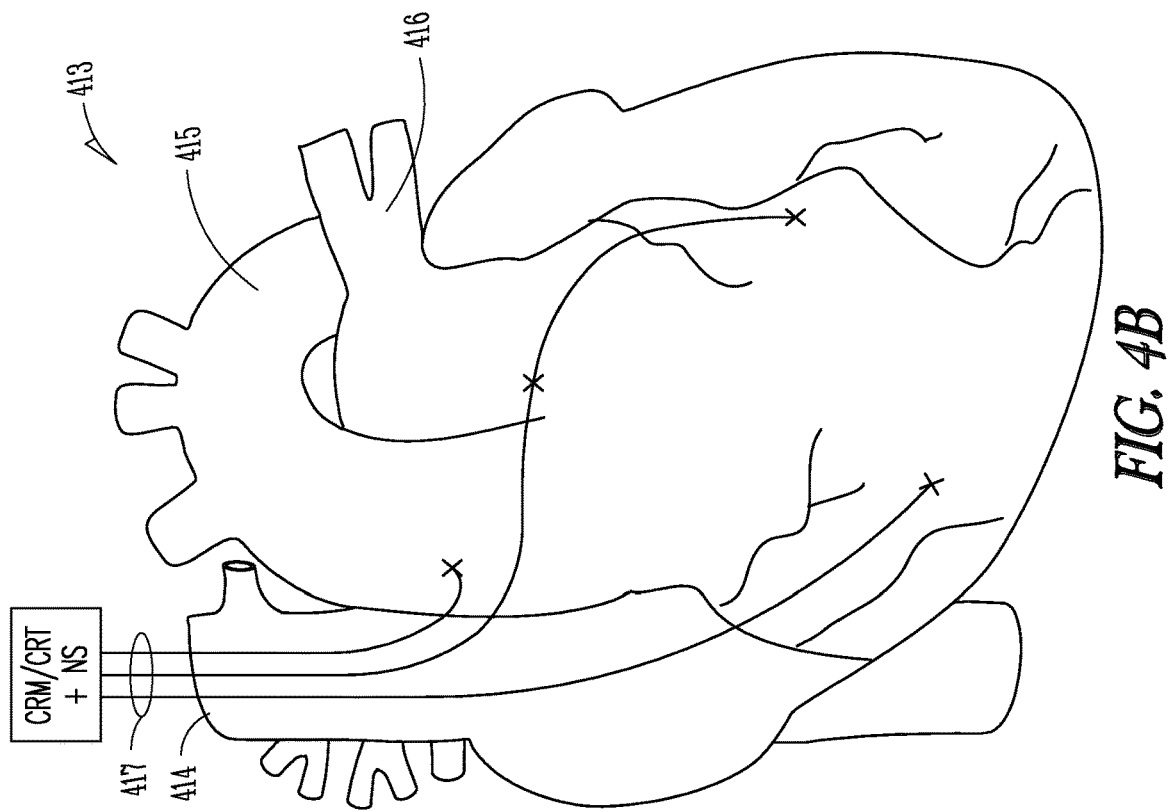
FIG. 4A illustrates transvascularly fed leads.
Figure 4B:
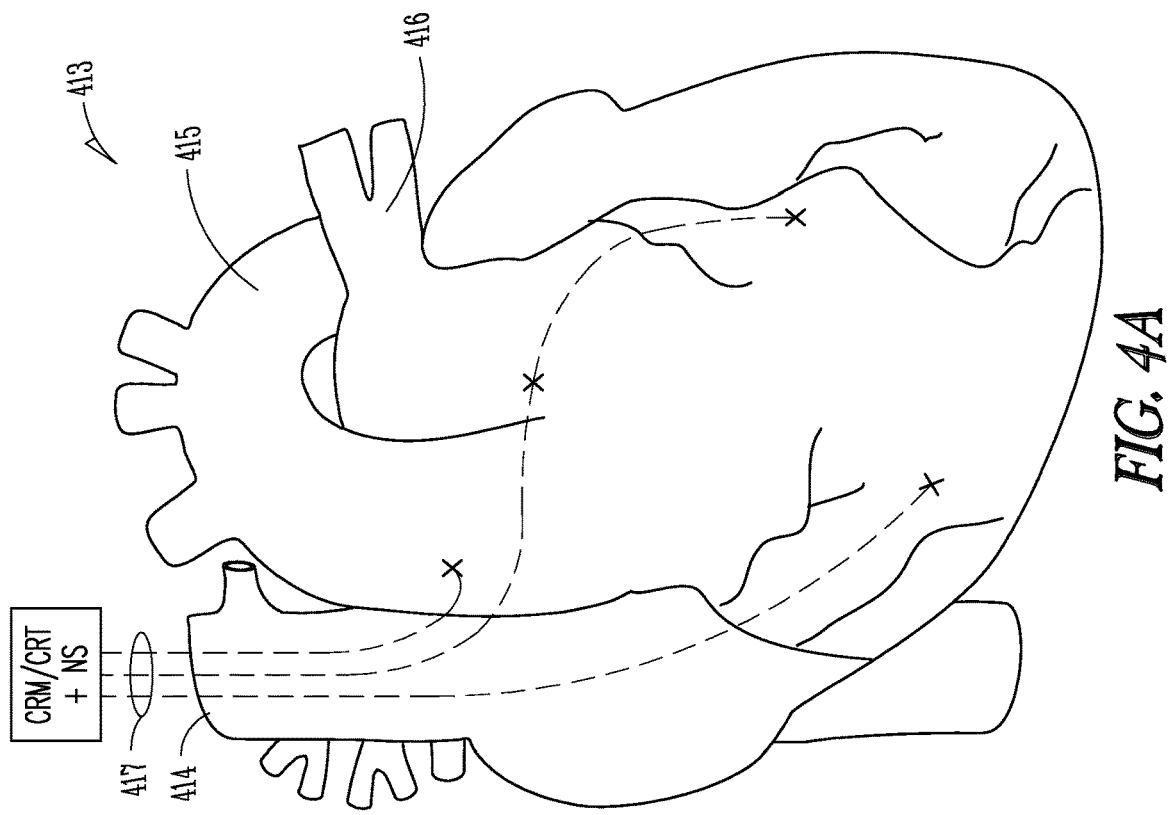
FIG. 4B illustrates epicardial leads for a heart, which may be used in some therapies.

As illustrated in FIGS. 4A and 4B, the heart 413 includes a superior vena cava 414, an aortic arch 415, and a pulmonary artery 416. CRM leads 417 pass nerve sites that can be stimulated in accordance with the present subject matter. FIG. 4A illustrates transvascularly fed leads, and FIG. 4B illustrates epicardial leads. Examples of electrode positions are provided in the drawings by the symbol "X". For example, CRM leads are capable of being intravascularly inserted through a peripheral vein and into the coronary sinus, and are capable of being intravascularly inserted through a peripheral vein and through the tricuspid valve into the right ventricle of the heart (not expressly shown in the figure) similar to a cardiac pacemaker lead, and continue from the right ventricle through the pulmonary valve into the pulmonary artery. The coronary sinus and pulmonary artery are provided as examples of vasculature proximate to the heart in which a lead can be intravascularly inserted to stimulate nerves within or proximate to the vasculature. Thus, according to various aspects of the present subject matter, nerves are stimulated in or around vasculature located proximate to the heart by at least one electrode intravascularly inserted therein.

FIGS. 5A and 5B illustrate the right side and left side of the heart, respectively, and further illustrate cardiac fat pads which provide neural targets for some neural stimulation therapies. FIG. 5A illustrates the right atrium 518, right ventricle 519, sinoatrial node 520, superior vena cava 514, inferior vena cava 521, aorta 522, right pulmonary veins 523, and right pulmonary artery 524. FIG. 5A also illustrates a cardiac fat pad 525 between the superior vena cava and aorta. Neural targets in the cardiac fat pad 525 are stimulated in some embodiments using an electrode screwed into or otherwise placed in the fat pad, and are stimulated in some embodiments using an intravenously-fed lead proximately positioned to the fat pad in a vessel such as the right pulmonary artery or superior vena cava, for example. FIG.

5B illustrates the left atrium 526, left ventricle 527, right atrium 518, right ventricle 519, superior vena cava 514, inferior vena cava 521, aorta 522, right pulmonary veins 523, left pulmonary vein 528, right pulmonary artery 524, and coronary sinus 529. FIG. 5B also illustrates a cardiac fat pad 530 located proximate to the right cardiac veins and a cardiac fat pad 531 located proximate to the inferior vena cava and left atrium. Neural targets in the fat pad 530 are stimulated in some embodiments using an electrode screwed into the fat pad 530, and are stimulated in some embodiments using an intravenously-fed lead proximately positioned to the fat pad in a vessel such as the right pulmonary artery 524 or right pulmonary vein 523, for example. Neural targets in the fat pad 531 are stimulated in some embodiments using an electrode screwed into the fat pad 531, and are stimulated in some embodiments using an intravenously-fed lead proximately positioned to the fat pad in a vessel such as the inferior vena cava 521 or coronary sinus or a lead in the left atrium 526, for example.

Various lead embodiments implement a number of designs, including an expandable stent-like electrode with a mesh surface dimensioned to abut a wall of a predetermined blood vessel, a coiled electrode(s), a fixed screw-type electrode(s), and the like. Various embodiments place the electrode(s) inside the blood vessel, into the wall of the blood vessel, or a combination of at least one electrode inside the blood vessel and at least one electrode into the wall of the blood vessel. The neural stimulation electrode(s) can be integrated into the same lead used for CRT or in another lead in addition to CRT lead(s).

Intravascularly-fed leads adapted to transvascularly stimulate a target outside of the vessel, also referred to herein as transvascular leads, can be used to stimulate other nerve sites. For example, an embodiment feeds a transvascular stimulation lead into the right azygos vein to stimulate and/or inhibit nerve traffic on the vagus nerve; and an embodiment feeds a transvascular stimulation lead into the internal jugular vein to stimulate and/or inhibit nerve traffic on the vagus nerve. Various embodiments use at least one lead intravascularly fed along a lead path to transvascularly apply neural stimulation and electrically stimulate a cardiac muscle, such as ventricular pacing, as part of CRT.

Other transvascular locations have been mentioned with respect to FIGS. 5A and 5B. Depending on the intravascular location of the neural stimulation electrode(s), the right vagal branch, the left vagal branch or a combination of the right and left vagal branches are capable of being stimulated. The left and right vagal branches innervate different areas of the heart, and thus provide different results when stimulated. According to present knowledge, the right vagus nerve appears to innervate the right side of the heart, including the right atrium and right ventricle, and the left vagus nerve appears to innervate the left side of the heart, including the left atrium and left ventricle. Stimulation of the right vagus has more chronotropic effects because the sinus node is on the right side of the heart. Thus, various embodiments selectively stimulate the right vagus nerve and/or the left vagus nerve to selectively control contractility, excitability, and inflammatory response on the right and/or left side of the heart. Since the venous system is for the most part symmetrical, leads can be fed into an appropriate vessel to transvascularly stimulate the right or left vagus nerve. For example, a lead in the right internal jugular vein can be used to stimulate the right vagus nerve and a lead in the left internal jugular vein can be used to stimulate the left vagus nerve.

The stimulation electrode(s) are not in direct neural contact with the nerve when the transvascular approach to peripheral nerve stimulation is used. Thus, problems associated with neural inflammation and injury commonly associated with direct contact electrodes are reduced.

Hypertension

As discussed above, hypertension can contribute to heart failure. One neural stimulation therapy involves treating hypertension by stimulating the baroreflex for sustained periods of time sufficient to reduce hypertension. The baroreflex is a reflex that can be triggered by stimulation of a baroreceptor or an afferent nerve trunk. Baroreflex neural targets include any sensor of pressure changes, such as sensory nerve endings in the wall of the auricles of the heart, cardiac fat pads, vena cava, aortic arch and carotid sinus, that is sensitive to stretching of the wall resulting from increased pressure from within, and that functions as the receptor of the central reflex mechanism that tends to reduce that pressure. Examples of afferent nerve trunks that can serve as baroreflex neural targets include the vagus, aortic and carotid nerves. Stimulating baroreceptors inhibits sympathetic nerve activity (stimulates the parasympathetic nervous system) and reduces systemic arterial pressure by decreasing peripheral vascular resistance and cardiac contractility. Baroreceptors are naturally stimulated by internal pressure and the stretching of the arterial wall. Some aspects of the present subject matter locally stimulate specific nerve endings in arterial walls rather than stimulate afferent nerve trunks in an effort to stimulate a desire response (e.g. reduced hypertension) while reducing the undesired effects of indiscriminate stimulation of the nervous system. For example, some embodiments stimulate baroreceptor sites in the pulmonary artery. Some embodiments of the present subject matter involve stimulating either baroreceptor sites or nerve endings in the aorta, the chambers of the heart, the fat pads of the heart, and some embodiments of the present subject matter involve stimulating an afferent nerve trunk, such as the vagus, carotid and aortic nerves. Some embodiments stimulate afferent nerve trunks using a cuff electrode, and some embodiments stimulate afferent nerve trunks using an intravascular lead positioned in a blood vessel proximate to the nerve, such that the electrical stimulation passes through the vessel wall to stimulate the afferent nerve trunk.

Myocardial Stimulation Therapies

Various embodiments use HF status as feedback for a myocardial stimulation therapy. For example, some embodiments provide or adjust CRT in response to a HF status index. Various embodiments also include or integrate myocardial stimulation with neural stimulation therapies. Some of these myocardial therapies are discussed below.

Bradycardia Pacing/CRT Pacing

A pacemaker is a device which paces the heart with timed pacing pulses, most commonly for the treatment of bradycardia where the ventricular rate is too slow. Atrio-ventricular conduction defects (i.e., AV block) and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate.

Implantable devices have also been developed that affect the manner and degree to which the heart chambers contract during a cardiac cycle in order to promote the efficient pumping of blood. The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Pathology of these conduction pathways and other inter-ventricular or intra-ventricular conduction deficits can be a causative factor in heart failure, which refers to a clinical syndrome in which an abnormality of cardiac function causes cardiac output to fall below a level adequate to meet the metabolic demand of peripheral tissues. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. Currently, a common form of CRT applies stimulation pulses to both ventricles, either simultaneously or separated by a specified biventricular offset interval, and after a specified atrio-ventricular delay interval with respect to the detection of an intrinsic atrial contraction or delivery of an atrial pace.

Anti-Tachycardia Therapy

Cardioversion, an electrical shock delivered to the heart synchronously with the QRS complex, and defibrillation, an electrical shock delivered without synchronization to the QRS complex, can be used to terminate most tachyarrhythmias. The electric shock terminates the tachyarrhythmia by simultaneously depolarizing the myocardium and rendering it refractory. A class of CRM devices known as an implantable cardioverter defibrillator (ICD) provides this kind of therapy by delivering a shock pulse to the heart when the device detects tachyarrhythmias. Another type of electrical therapy for tachycardia is anti-tachycardia pacing (ATP). In ventricular ATP, the ventricles are competitively paced with one or more pacing pulses in an effort to interrupt the reentrant circuit causing the tachycardia. Modern ICDs typically have ATP capability, and deliver ATP therapy or a shock pulse when a tachyarrhythmia is detected.

Therapy for Cardiac Remodeling

CRT can be beneficial in reducing the deleterious ventricular remodeling which can occur in post-MI and heart failure patients. Presumably, this occurs as a result of changes in the distribution of wall stress experienced by the ventricles during the cardiac pumping cycle when CRT is applied. The degree to which a heart muscle fiber is stretched before it contracts is termed the preload, and the maximum tension and velocity of shortening of a muscle fiber increases with increasing preload. When a myocardial region contracts late relative to other regions, the contraction of those opposing regions stretches the later contracting region and increases the preload. The degree of tension or stress on a heart muscle fiber as it contracts is termed the afterload. Because pressure within the ventricles rises rapidly from a diastolic to a systolic value as blood is pumped out into the aorta and pulmonary arteries, the part of the ventricle that first contracts due to an excitatory stimulation pulse does so against a lower afterload than does a part of the ventricle contracting later. Thus a myocardial region which contracts later than other regions is subjected to both an increased preload and afterload. This situation is created frequently by the ventricular conduction delays associated with heart failure and ventricular dysfunction due to an MI. The increased wall stress to the late-activating myocardial regions is most probably the trigger for ventricular remodeling. By pacing one or more sites in a ventricle in a manner which causes a more coordinated contraction, CRT provides pre-excitation of myocardial regions which would otherwise be activated later during systole and experience increased wall stress. The pre-excitation of the remodeled region relative to other regions unloads the region from mechanical stress and allows reversal or prevention of remodeling to occur.

Device Embodiments

Figure 6:
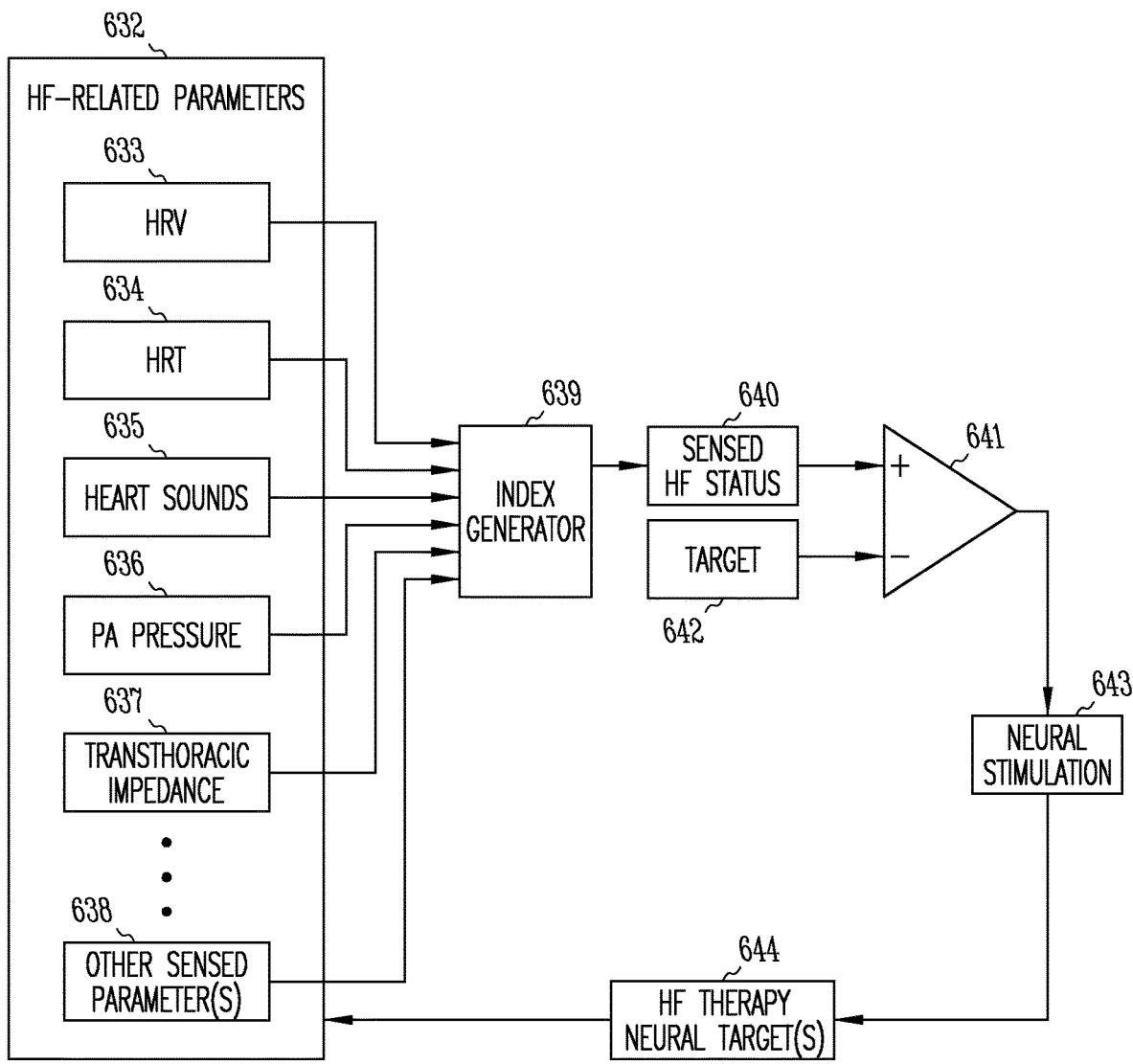
FIG. 6 illustrates a device embodiment to generate a sensed HF status index using two or more HF-related parameters and controlling neural stimulation to an HF-therapy neural target.

FIG. 6 illustrates a device embodiment to generate a sensed HF status index using two or more HF-related parameters and controlling neural stimulation to an HF-therapy neural target. In the illustrated device embodiment, a number of HF-related parameters 632 are able to be measured. Examples include HRV 633, HRT 634, heart sounds 635, pulmonary artery pressure 636 and/or other blood pressure, transthoracic impedance 637 or other sensed parameter(s) 638. These measured HF-related parameters are received by an index generator 639, which generates a sensed HF status index 640 as a function of at least two measured parameters 632 or otherwise using at least two measured parameters 632. A comparator 641 compares the index 640 to a target 642 for the index. The target can be a programmed value. The result of the comparison is used to control the neural stimulation 643, which is applied to the HF therapy neural target(s) 644. In various embodiments, the neural stimulation can stimulate parasympathetic activity and/or inhibit sympathetic neural activity to elicit a parasympathetic response for chronic HF therapy. In various embodiments, the neural stimulation can stimulate sympathetic activity and/or inhibit parasympathetic activity to elicit a sympathetic response, such as may be desirable as a short term therapy in response to an event to maintain cardiac output until the patient can travel to a clinical setting.

Figure 7:
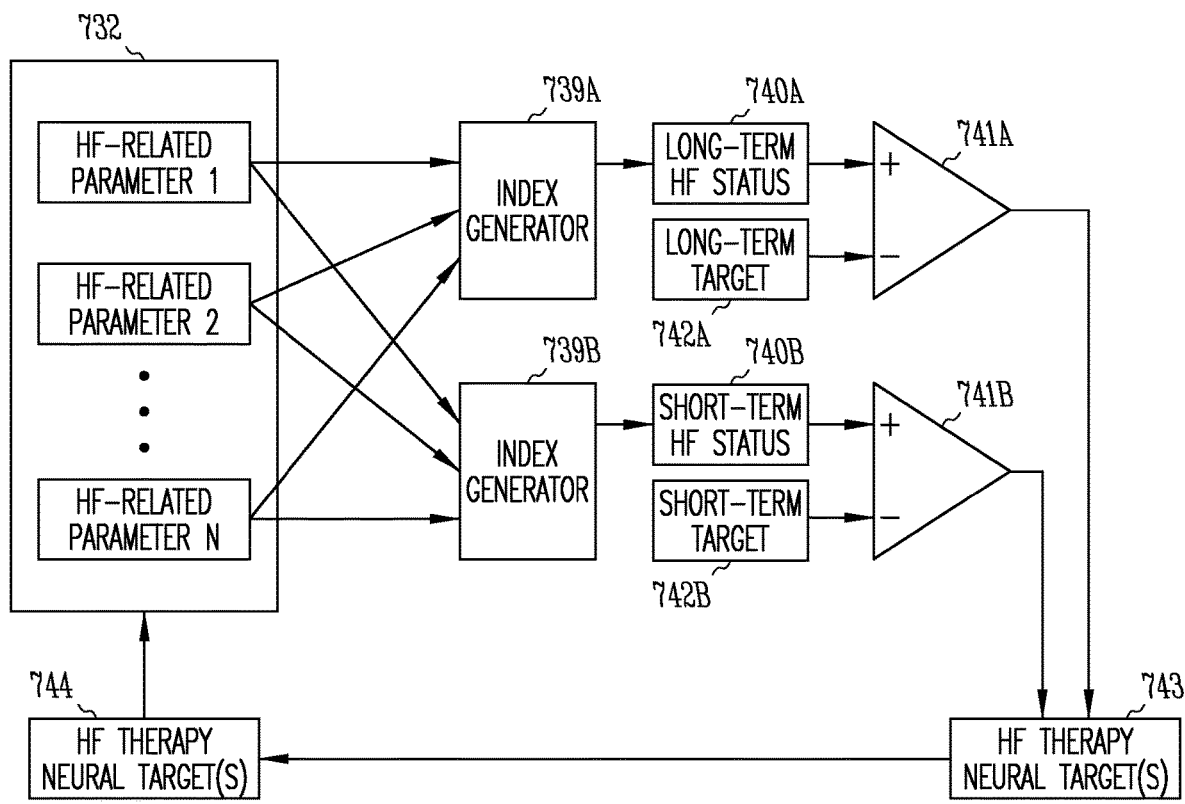
FIG. 7 illustrates a device embodiment to generate a chronic or long-term sensed HF status index and an acute or short-term sensed HF status index using two or more HF-related parameters, and controlling neural stimulation to an HF-therapy neural target using the indices.

FIG. 7 illustrates a device embodiment to generate a chronic or long-term sensed HF status index and an acute or short-term sensed HF status index using two or more HF-related parameters, and controlling neural stimulation to an HF-therapy neural target using the indices. Measured HF-related parameters are received by a long-term index generator 739A, which generates a long-term sensed HF status index 740A as a function of at least two measured parameters 732 or otherwise using at least two measured parameters 732. A comparator 741A compares the index 740A to a target 742A for the index. The target can be a programmed value. In various embodiments, the target is based on an average or trend of a number of previous values for the index, such that the comparator is able to determine if the index value is trending higher or lower. The result of the comparison is used as chronic feedback for the neural stimulation 743, which is applied to the HF therapy neural target(s) 744. For example, the long-term HF status index can be used to adjust an intensity, duration or location of neural stimulation to increase or decrease a parasympathetic response as part of a HF therapy. Measured HF-related parameters are received by a short-term index generator 739B, which generates a short-term sensed HF status index 740B as a function of at least two measured parameters 732 or otherwise using at least two measured parameters 732. A comparator 741B compares the index 740B to a target 742B for the index. The target can be a programmed value. In various embodiments, the target is based on an average or trend of a number of previous values for the index, such that the comparator is able to determine if the index value is trending higher or lower. The result of the comparison is used as short-term feedback for the neural stimulation 743, which is applied to the HF therapy neural target(s) 744. For example, the long-term HF status index can be used to adjust an intensity, duration or location of neural stimulation to increase or decrease a sympathetic response as part of an acute HF therapy due to a decompensation event.

Figure 8:
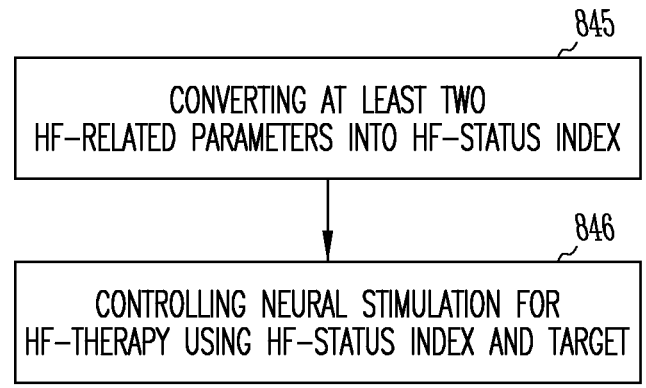
FIG. 8 illustrates a method for controlling an HF therapy, according to various embodiments of the present subject matter.

FIG. 8 illustrates a method for controlling an HF therapy, according to various embodiments of the present subject matter. The device embodiment of FIG. 6, for example, is capable of performing this method. At 845, at least two HF-related parameters are converted into a HF-status index. At 846, the neural stimulation for a HF-therapy is controlled using the HF-status index and a target for the index.

Figure 9:
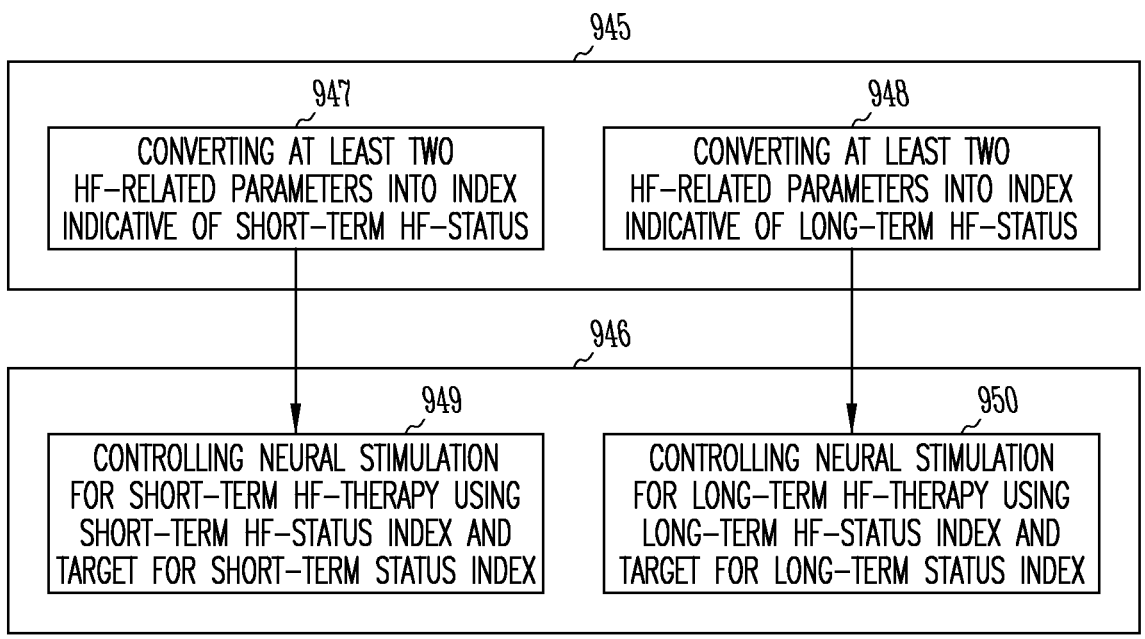
FIG. 9 illustrates a method for controlling an HF therapy, according to various embodiments of the present subject matter.
Figure 10:
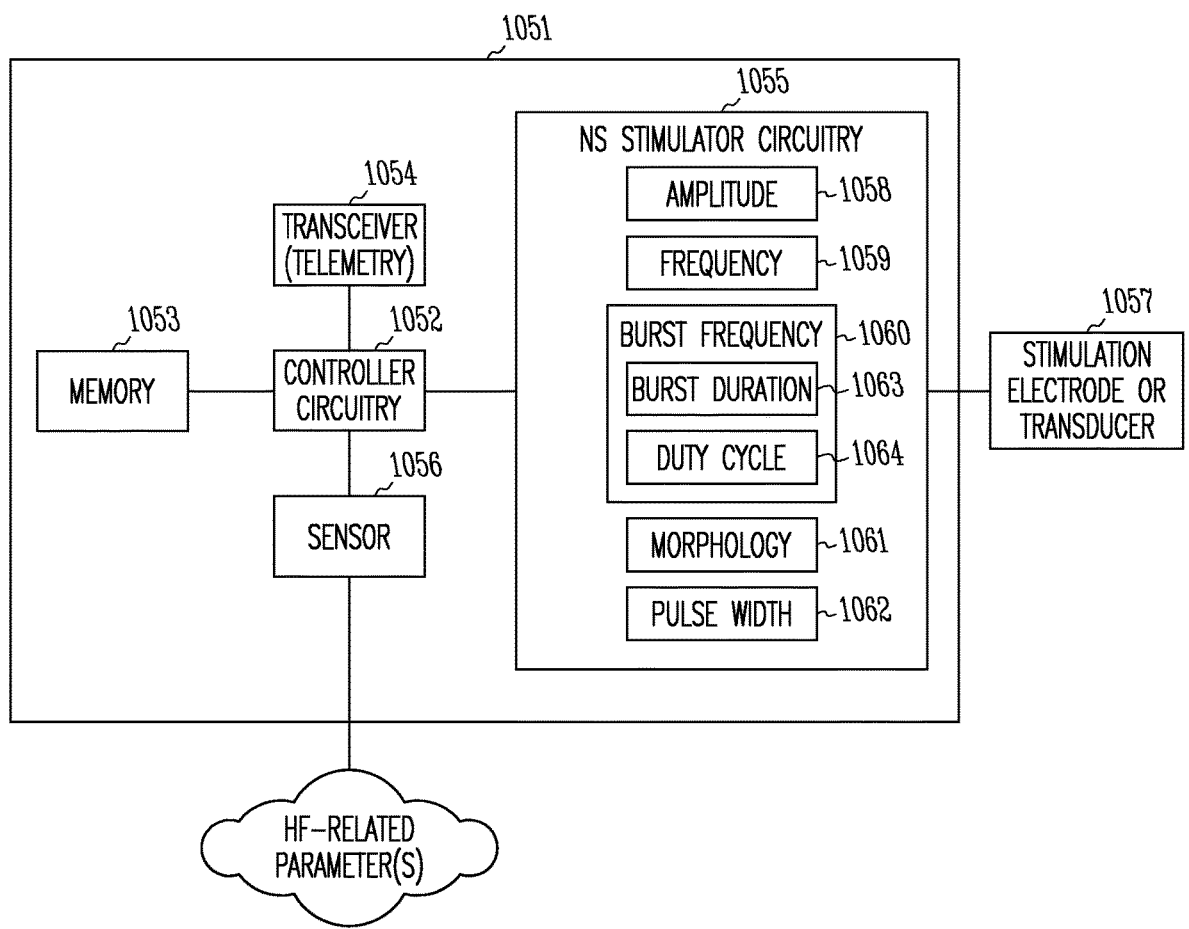
FIG. 10 illustrates an implantable medical device (IMD), according to various embodiments of the present subject matter.

FIG. 9 illustrates a method for controlling an HF therapy, according to various embodiments of the present subject matter. The device embodiment of FIG. 7, for example, is capable of performing this method. The boxes 945 and 946 in FIG. 9 generally correspond to 845 and 846 in FIG. 8. At 947, at least two HF-related parameters are converted into index indicative of a short-term HF-status; and at 948, at least two HF-related parameters are converted into index indicative of a long-term HF-status. At 949, the neural stimulation for a short-term HF-therapy is controlled using the short-term HF-status index and a target for the short-term index; and at 950, the neural stimulation for a long-term HF-therapy is controlled using the long-term HF-status index and a target for the long-term index. Short-term indexes can be based on recent measured HF-related parameters, such as parameters measured in the past minute or hour. Long-term indexes can be based on parameters measured over a longer period of time, such as hours, days, weeks and months, for example . . . . FIG. 10 illustrates an implantable medical device (IMD) 1051, according to various embodiments of the present subject matter. The illustrated IMD provides neural stimulation signals for delivery to predetermined neural targets to provide heart failure therapy. The illustrated device includes controller circuitry 1052 and memory 1053. The controller circuitry is capable of being implemented using hardware, software, and combinations of hardware and software. For example, according to various embodiments, the controller circuitry includes a processor to perform instructions embedded in the memory to perform functions associated with the neural stimulation therapy. For example, the illustrated device further includes a transceiver 1054 and associated circuitry for use to communicate with a programmer or another external or internal device. Various embodiments have wireless communication capabilities. For example, some transceiver embodiments use a telemetry coil to wirelessly communicate with a programmer or another external or internal device.

The illustrated device further includes neural stimulation circuitry 1055. Various embodiments of the device also includes sensor circuitry 1056. According to some embodiments, one or more leads are able to be connected to the sensor circuitry and neural stimulation circuitry. Some embodiments use wireless connections between the sensor (s) and sensor circuitry, and some embodiments use wireless connections between the stimulator circuitry and electrodes. According to various embodiments, the neural stimulation circuitry is used to apply electrical stimulation pulses to desired neural targets, such as through one or more stimulation electrodes 1057 positioned at predetermined location (s). Some embodiments use transducers to provide other types of energy, such as ultrasound, light or magnetic energy. In various embodiments, the sensor circuitry is used to detect physiological responses. Examples of physiological responses include cardiac activity, such as heart rate and minute ventilation, blood pressure, and respiration, such as tidal volume and minute ventilation, as well as sensed HRV and HRT data. The controller circuitry can compare a target range (or ranges) of the sensed physiological response(s) stored in the memory to the sensed physiological response(s) to appropriately adjust the intensity of the neural stimulation/inhibition.

According to various embodiments, the stimulation circuitry 1055 includes modules to set or adjust any one or any combination of two or more of the following pulse features: the amplitude 1058 of the stimulation pulse, the frequency 1059 of the stimulation pulse, the burst frequency 1060 of the pulse, the wave morphology 1061 of the pulse, and the pulse width 1062. The illustrated burst frequency 1060 pulse feature includes burst duration 1063 and duty cycle 1064, which can be adjusted as part of a burst frequency pulse feature or can be adjusted separately. For example, a burst frequency can refer to the number of bursts per minute. Each of these bursts has a burst duration (an amount of time bursts of stimulation are provided) and a duty cycle (a ratio of time where stimulation is provided to total time). Thus, by way of example and not limitation, six bursts can be delivered during a one minute stimulation time (burst duration), where the length (pulse width) of each burst is five seconds and the time period between bursts is five seconds. In this example, the burst frequency is six burst per minute, the burst duration is 60 seconds, and the duty cycle is 50% ((6 bursts×5 sec./burst)/60 seconds). Additionally, the duration of one or more bursts can be adjusted without reference to any steady burst frequency. For example, a single stimulation burst of a predetermined burst duration or a pattern of bursts of predetermined pulse width(s) and burst timing can be provided in response to a sensed signal. Furthermore, the duty cycle can be adjusted by adjusting the number of bursts and/or adjusting the duration of one or more bursts, without requiring the bursts to be delivered with a steady burst frequency. Examples of wave morphology include a square wave, triangle wave, sinusoidal wave, and waves with desired harmonic components to mimic white noise such as is indicative of naturally-occurring baroreflex stimulation. Additionally, various controller embodiments are capable of controlling a duration of the stimulation. The sensor circuitry is used to detect HF-related parameters to create an HF status index. The controller compares the index to a target range stored in memory, and controls the neural stimulation based on the comparison in an attempt to keep the response within the target range. The target range can be programmable and/or derived from past measurements.

Figure 11:
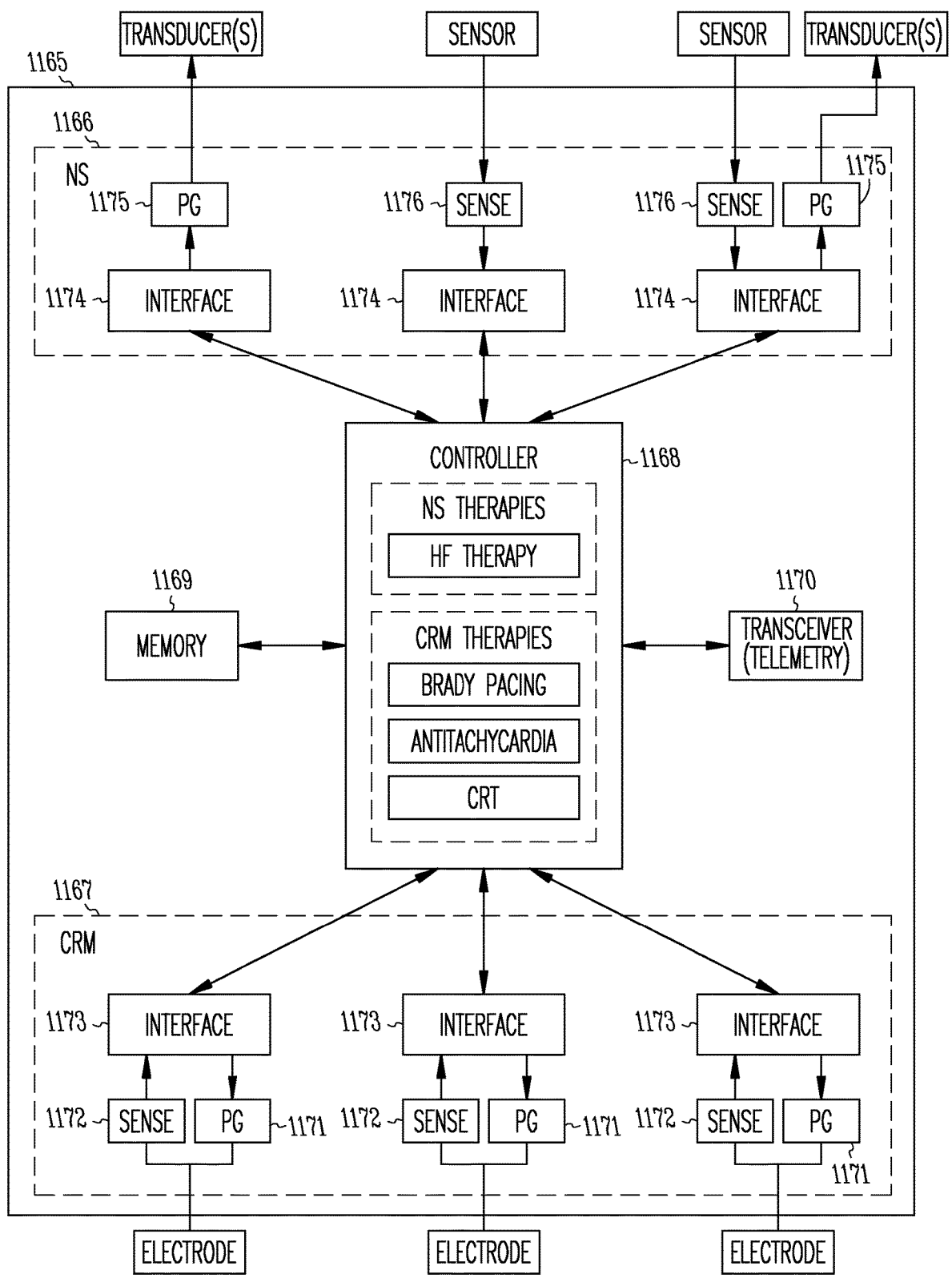
FIG. 11 illustrates an implantable medical device (IMD) having a neural stimulation (NS) component and cardiac rhythm management (CRM) component, according to various embodiments of the present subject matter.

FIG. 11 illustrates an implantable medical device (IMD) 1165 having a neural stimulation (NS) component 1166 and cardiac rhythm management (CRM) component 1167, according to various embodiments of the present subject matter. The illustrated device includes a controller 1168 and memory 1169. According to various embodiments, the controller includes hardware, software, or a combination of hardware and software to perform the neural stimulation and CRM functions. For example, the programmed therapy applications discussed in this disclosure are capable of being stored as computer-readable instructions embodied in memory and executed by a processor. According to various embodiments, the controller includes a processor to execute instructions embedded in memory to perform the neural stimulation and CRM functions. The neural stimulation therapy includes a heart failure therapy. Various embodiments include anti-hypertension (AHT) therapy and anti-remodeling therapy (ART). Examples of CRM functions include bradycardia pacing, anti-tachycardia therapies such as ATP, defibrillation and cardioversion, and CRT. The controller also executes instructions to detect a tachyarrhythmia. The illustrated device further includes a transceiver 1170 and associated circuitry for use to communicate with a programmer or another external or internal device. Various embodiments include a telemetry coil.

The CRM therapy section 1167 includes components, under the control of the controller, to stimulate a heart and/or sense cardiac signals using one or more electrodes. The illustrated CRM therapy section includes a pulse generator 1171 for use to provide an electrical signal through an electrode to stimulate a heart, and further includes sense circuitry 1172 to detect and process sensed cardiac signals. An interface 1173 is generally illustrated for use to communicate between the controller 1168 and the pulse generator 1171 and sense circuitry 1172. Three electrodes are illustrated as an example for use to provide CRM therapy. However, the present subject matter is not limited to a particular number of electrode sites. Each electrode may include its own pulse generator and sense circuitry. However, the present subject matter is not so limited. The pulse generating and sensing functions can be multiplexed to function with multiple electrodes.

The NS therapy section 1166 includes components, under the control of the controller, to stimulate a neural stimulation target and/or sense parameters associated with nerve activity or surrogates of nerve activity such as blood pressure and respiration. Three interfaces 1174 are illustrated for use to provide neural stimulation. However, the present subject matter is not limited to a particular number interfaces, or to any particular stimulating or sensing functions. Pulse generators 1175 are used to provide electrical pulses to transducer or transducers for use to stimulate a neural stimulation target. According to various embodiments, the pulse generator includes circuitry to set, and in some embodiments change, the amplitude of the stimulation pulse, the frequency of the stimulation pulse, the burst frequency of the pulse, and the morphology of the pulse such as a square wave, triangle wave, sinusoidal wave, and waves with desired harmonic components to mimic white noise or other signals. Sense circuits 1176 are used to detect and process signals from a sensor, such as a sensor of nerve activity, blood pressure, respiration, and the like. The interfaces 1174 are generally illustrated for use to communicate between the controller 1168 and the pulse generator 1175 and sense circuitry 1176. Each interface, for example, may be used to control a separate lead. Various embodiments of the NS therapy section only includes a pulse generator to stimulate a neural target.

Figure 12:
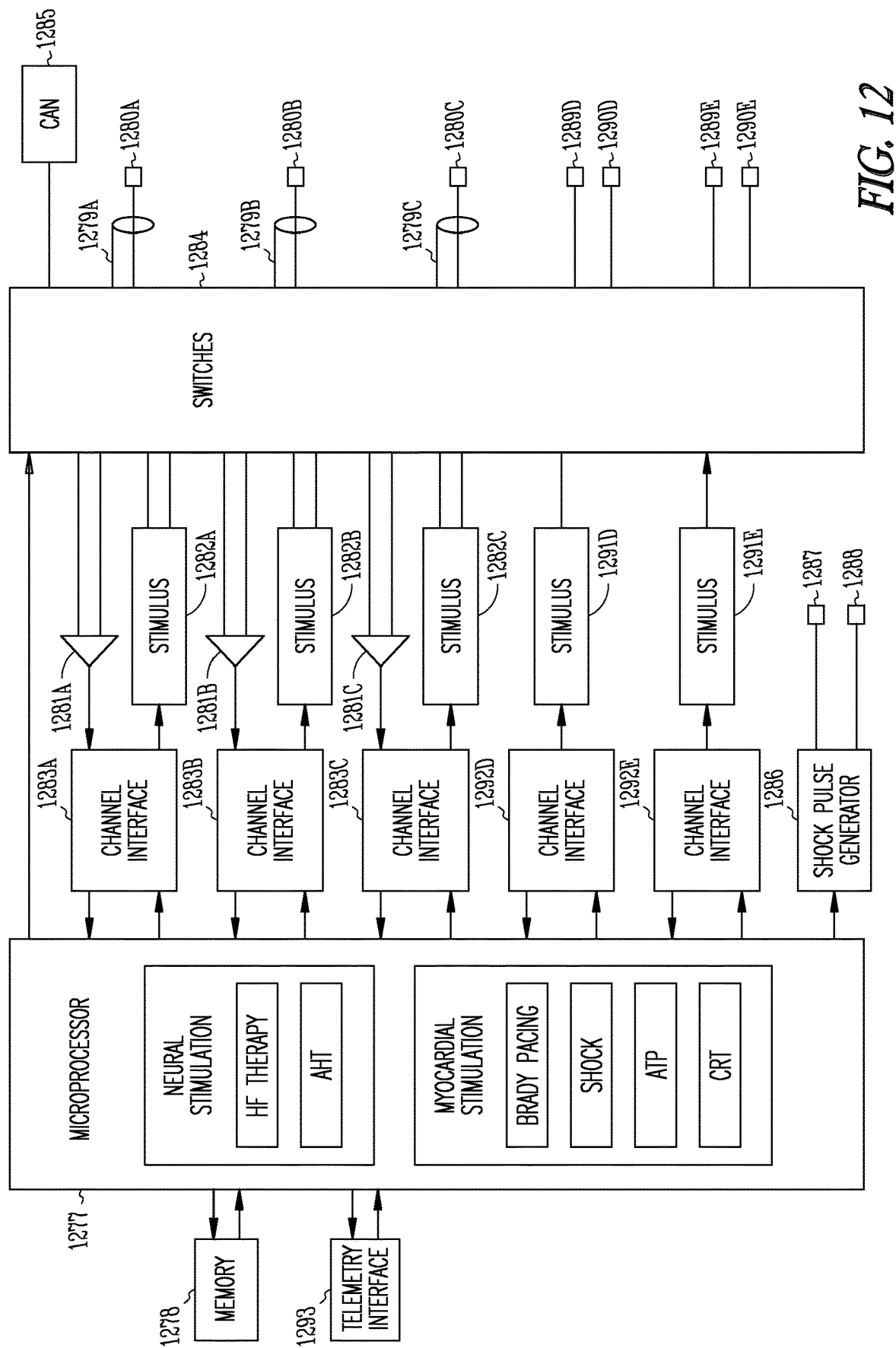
FIG. 12 shows a system diagram of an embodiment of a microprocessor-based implantable device, according to various embodiments.

FIG. 12 shows a system diagram of an embodiment of a microprocessor-based implantable device, according to various embodiments. The controller of the device is a microprocessor 1277 which communicates with a memory 1278 via a bidirectional data bus. The controller could be implemented by other types of logic circuitry (e.g., discrete components or programmable logic arrays) using a state machine type of design, but a microprocessor-based system is preferable. As used herein, the term "circuitry" should be taken to refer to either discrete logic circuitry or to the programming of a microprocessor. Shown in the figure are three examples of sensing and pacing channels designated "A" through "C" comprising bipolar leads with ring electrodes 1279A-C and tip electrodes 1280A-C, sensing amplifiers 1281A-C, pulse generators 1282A-C, and channel interfaces 1283A-C. Each channel thus includes a pacing channel made up of the pulse generator connected to the electrode and a sensing channel made up of the sense amplifier connected to the electrode. The channel interfaces 1283A-C communicate bidirectionally with the microprocessor 1277, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing. The intrinsic atrial and/or ventricular rates can be measured by measuring the time intervals between atrial and ventricular senses, respectively, and used to detect atrial and ventricular tachyarrhythmias.

The electrodes of each bipolar lead are connected via conductors within the lead to a switching network 1284 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing (can) 1285 or an electrode on another lead serving as a ground electrode. A shock pulse generator 1286 is also interfaced to the controller for delivering a defibrillation shock via a pair of shock electrodes 1287 and 1288 to the atria or ventricles upon detection of a shockable tachyarrhythmia.

Neural stimulation channels, identified as channels D and E, are incorporated into the device for delivering parasympathetic stimulation and/or sympathetic inhibition, where one channel includes a bipolar lead with a first electrode 1289D and a second electrode 1290D, a pulse generator 1291D, and a channel interface 1292D, and the other channel includes a bipolar lead with a first electrode 1289E and a second electrode 1290E, a pulse generator 1291E, and a channel interface 1292E. Other embodiments may use unipolar leads in which case the neural stimulation pulses are referenced to the can or another electrode. The pulse generator for each channel outputs a train of neural stimulation pulses which may be varied by the controller as to amplitude, frequency, duty-cycle, and the like. In this embodiment, each of the neural stimulation channels uses a lead which can be intravascularly disposed near an appropriate neural target. Other types of leads and/or electrodes may also be employed. A nerve cuff electrode may be used in place of an intravascularly disposed electrode to provide neural stimulation. In some embodiments, the leads of the neural stimulation electrodes are replaced by wireless links.

The figure illustrates a telemetry interface 1293 connected to the microprocessor, which can be used to communicate with an external device. The illustrated microprocessor 1277 is capable of performing neural stimulation therapy routines and myocardial stimulation routines. Examples of NS therapy routines include a heart failure therapy, an antihypertension therapy (AHT), and anti-remodeling therapy (ART). Examples of myocardial therapy routines include bradycardia pacing therapies, anti-tachycardia shock therapies such as cardioversion or defibrillation therapies, anti-tachycardia pacing therapies (ATP), and cardiac resynchronization therapies (CRT).

System Embodiments

Figure 13:
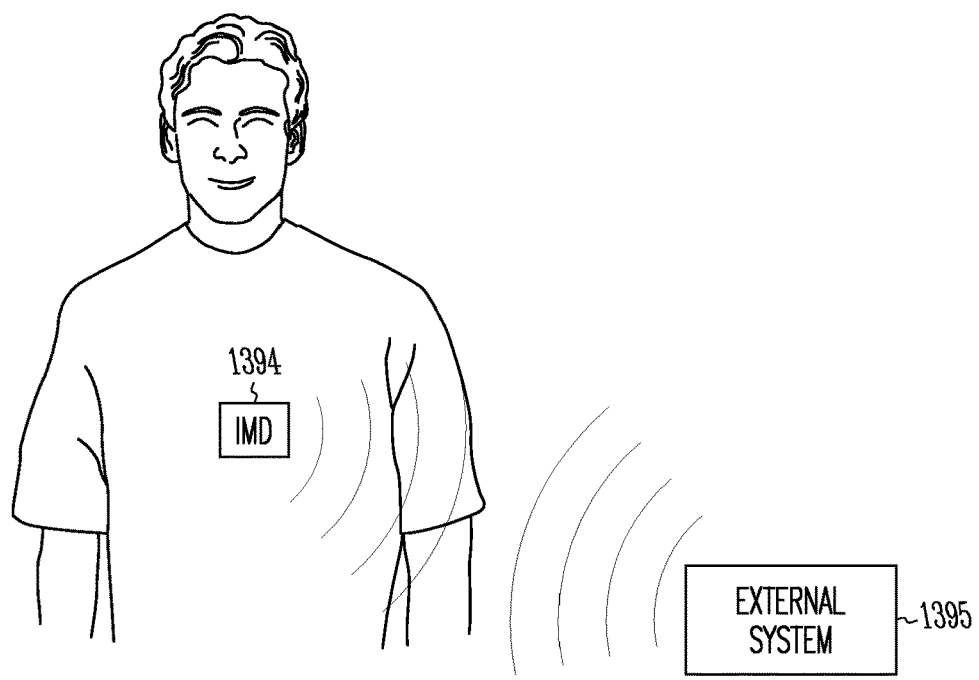
FIG. 13 illustrates a system including an implantable medical device (IMD) and an external system or device, according to various embodiments of the present subject matter.

FIG. 13 illustrates a system including an implantable medical device (IMD) 1394 and an external system or device 1395, according to various embodiments of the present subject matter. Various embodiments of the IMD include a combination of NS and CRM functions. The IMD may also deliver biological agents and pharmaceutical agents. The external system and the IMD are capable of wirelessly communicating data and instructions. In various embodiments, for example, the external system and IMD use telemetry coils to wirelessly communicate data and instructions. Thus, the programmer can be used to adjust the programmed therapy provided by the IMD, and the IMD can report device data (such as battery and lead resistance) and therapy data (such as sense and stimulation data) to the programmer using radio telemetry, for example. According to various embodiments, the IMD stimulates/inhibits a neural target to provide HF therapy.

The external system allows a user such as a physician or other caregiver or a patient to control the operation of the IMD and obtain information acquired by the IMD. In one embodiment, external system includes a programmer communicating with the IMD bi-directionally via a telemetry link. In another embodiment, the external system is a patient management system including an external device communicating with a remote device through a telecommunication network. The external device is within the vicinity of the IMD and communicates with the IMD bi-directionally via a telemetry link. The remote device allows the user to monitor and treat a patient from a distant location. The patient monitoring system is further discussed below.

The telemetry link provides for data transmission from implantable medical device to external system. This includes, for example, transmitting real-time physiological data acquired by IMD, extracting physiological data acquired by and stored in IMD, extracting therapy history data stored in implantable medical device, and extracting data indicating an operational status of the IMD (e.g., battery status and lead impedance). Telemetry link also provides for data transmission from external system to IMD. This includes, for example, programming the IMD to acquire physiological data, programming IMD to perform at least one self-diagnostic test (such as for a device operational status), and programming the IMD to deliver at least one therapy.

Figure 14:
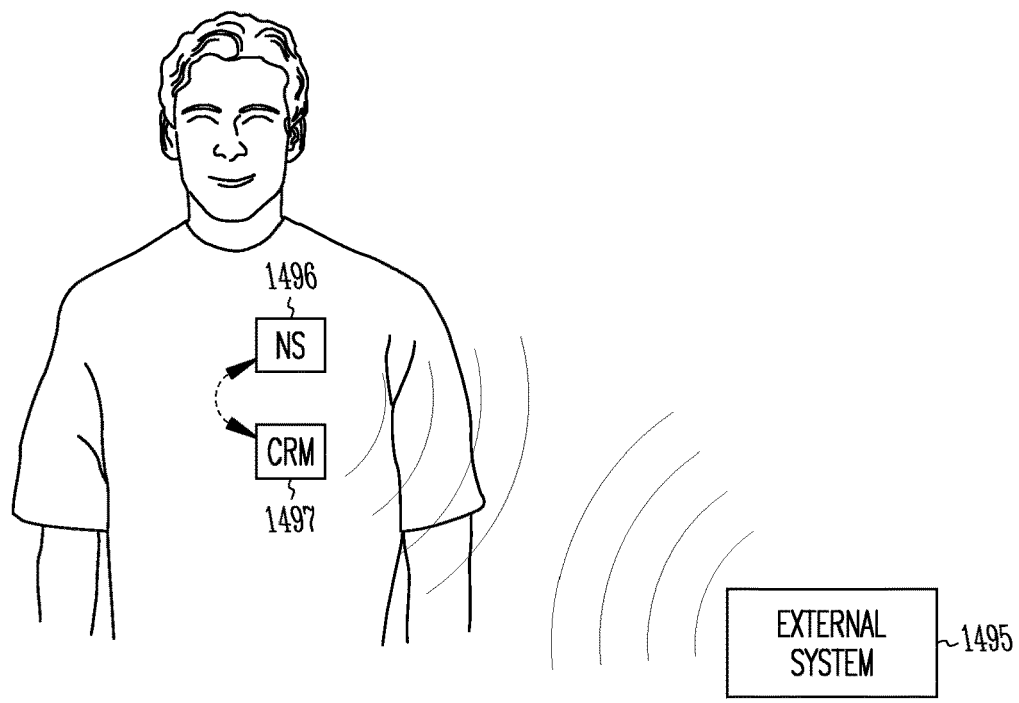
FIG. 14 illustrates a system including an external device, an implantable neural stimulator (NS) device and an implantable cardiac rhythm management (CRM) device, according to various embodiments of the present subject matter.

FIG. 14 illustrates a system including an external device 1495, an implantable neural stimulator (NS) device 1496 and an implantable cardiac rhythm management (CRM) device 1497, according to various embodiments of the present subject matter. Various aspects involve a method for communicating between an NS device and a CRM device or other cardiac stimulator. In various embodiments, this communication allows one of the devices 1496 or 1497 to deliver more appropriate therapy (i.e. more appropriate NS therapy or CRM therapy) based on data received from the other device. Some embodiments provide on-demand communications. In various embodiments, this communication allows each of the devices to deliver more appropriate therapy (i.e. more appropriate NS therapy and CRM therapy) based on data received from the other device. The illustrated NS device and the CRM device are capable of wirelessly communicating with each other, and the external system is capable of wirelessly communicating with at least one of the NS and the CRM devices. For example, various embodiments use telemetry coils to wirelessly communicate data and instructions to each other. In other embodiments, communication of data and/or energy is by ultrasonic means. Rather than providing wireless communication between the NS and CRM devices, various embodiments provide a communication cable or wire, such as an intravenously-fed lead, for use to communicate between the NS device and the CRM device. In some embodiments, the external system functions as a communication bridge between the NS and CRM devices.

Figure 15:
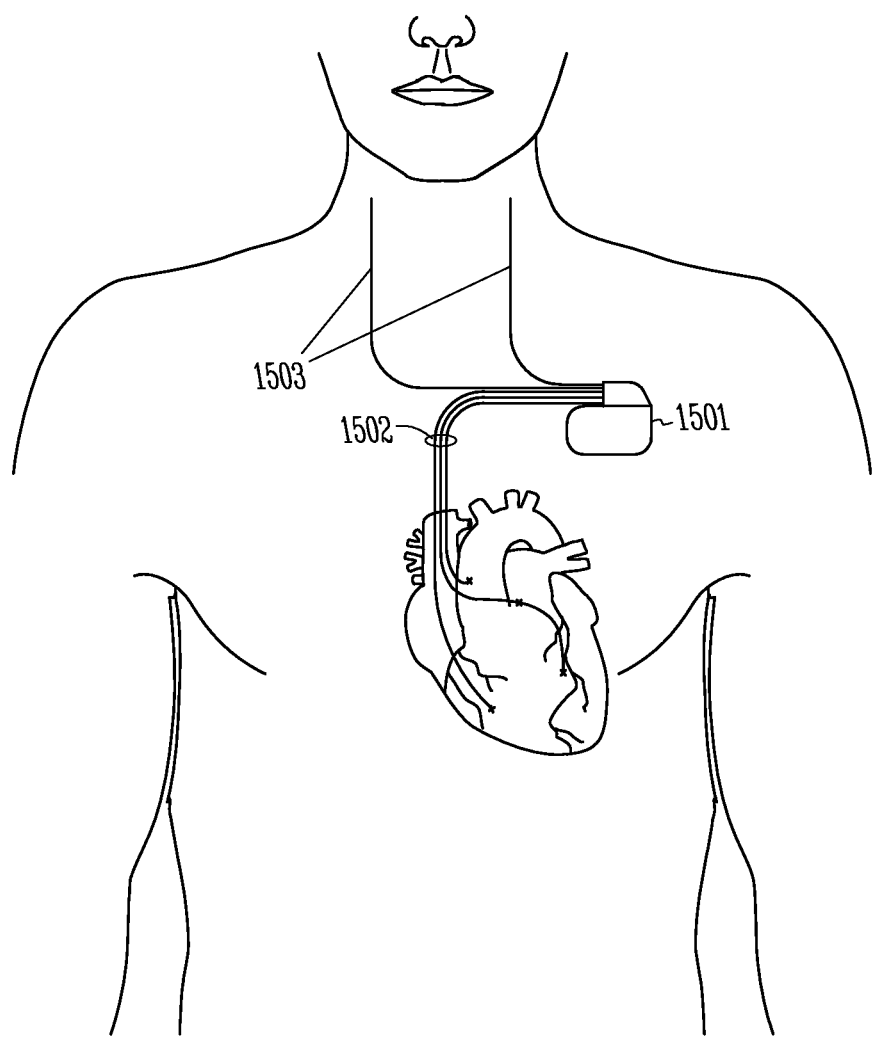
FIG. 15 illustrates an IMD placed subcutaneously or submuscularly in a patient's chest with lead(s) positioned to provide a CRM therapy to a heart, and with lead(s) positioned to stimulate and/or inhibit neural traffic in a vagus nerve, by way of example and not by way of limitation, according to various embodiments.

FIG. 15 illustrates an IMD 1501 placed subcutaneously or submuscularly in a patient's chest with lead(s) 1502 positioned to provide a CRM therapy to a heart, and with lead(s) 1503 positioned to stimulate and/or inhibit neural traffic in a vagus nerve, by way of example and not by way of limitation, according to various embodiments. According to various embodiments, neural stimulation lead(s) 1503 are subcutaneously tunneled to a neural target, and can have a nerve cuff electrode to stimulate the neural target. Some lead embodiments are intravascularly fed into a vessel proximate to the neural target, and use transducer(s) within the vessel to transvascularly stimulate the neural target. For example, some embodiments target the vagus nerve using electrode(s) positioned within the internal jugular vein.

Figure 16:
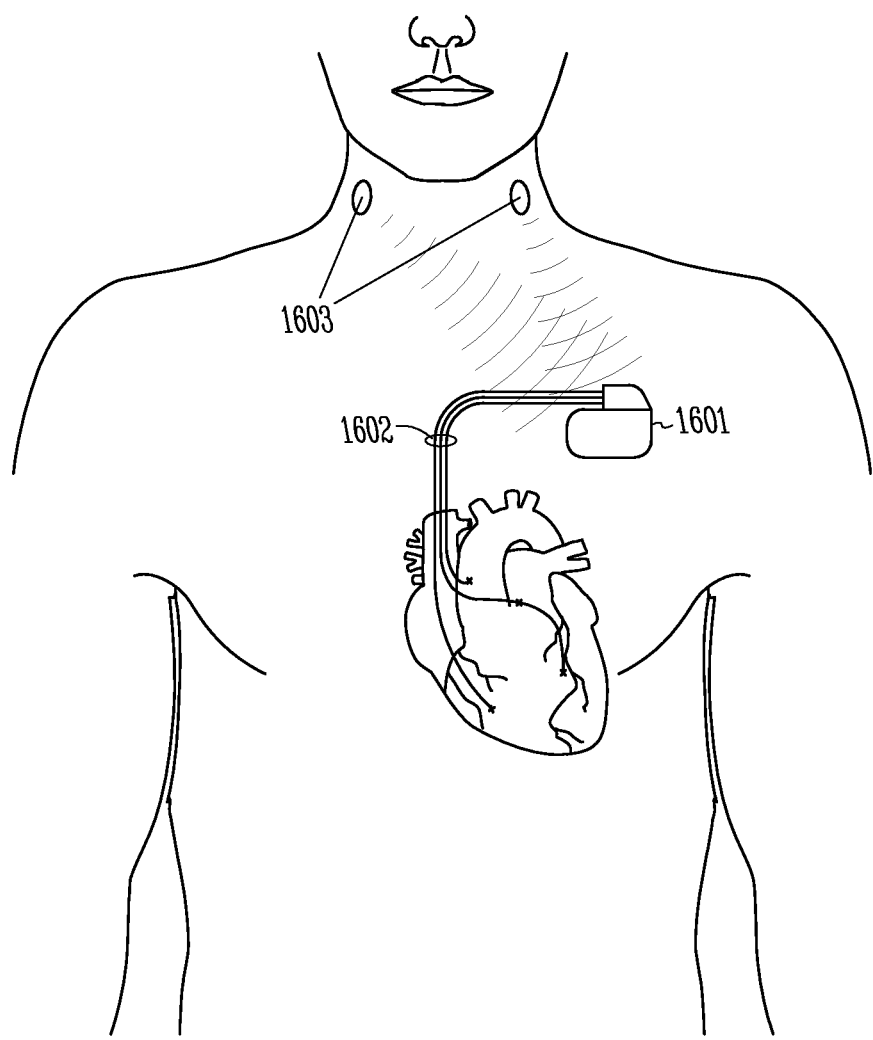
FIG. 16 illustrates an IMD with lead(s) positioned to provide a CRM therapy to a heart, and with satellite transducers positioned to stimulate/inhibit a neural target, according to various embodiments.

FIG. 16 illustrates an IMD 1601 with lead(s) 1602 positioned to provide a CRM therapy to a heart, and with satellite transducers 1603 positioned to stimulate/inhibit a neural target, according to various embodiments. The satellite transducers are connected to the IMD, which functions as the planet for the satellites, via a wireless link. Stimulation and communication can be performed through the wireless link. Examples of wireless links include RF links and ultrasound links. Although not illustrated, some embodiments perform myocardial stimulation using wireless links. Examples of satellite transducers include subcutaneous electrodes, nerve cuff electrodes and intravascular electrodes.

Figure 17:
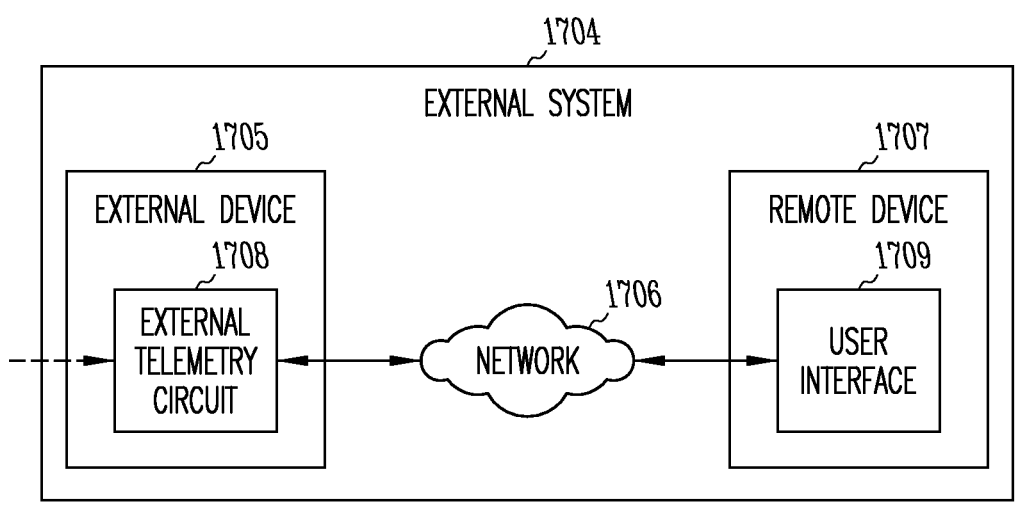
FIG. 17 is a block diagram illustrating an embodiment of an external system.

FIG. 17 is a block diagram illustrating an embodiment of an external system 1704. The external system includes a programmer, in some embodiments. In the illustrated embodiment, the external system includes a patient management system. As illustrated, the external system 1704 is a patient management system including an external device 1705, a telecommunication network 1706, and a remote device 1707. External device 1705 is placed within the vicinity of an IMD and includes external telemetry system 1708 to communicate with the IMD. Remote device(s) 1707 is in one or more remote locations and communicates with external device 1705 through network 1706, thus allowing a physician or other caregiver to monitor and treat a patient from a distant location and/or allowing access to various treatment resources from the one or more remote locations. The illustrated remote device 1707 includes a user interface 1709.

One of ordinary skill in the art will understand that the modules and other circuitry shown and described herein can be implemented using software, hardware, and combinations of software and hardware. As such, the term module is intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:

1. A method, comprising:
   delivering a therapy using an implantable device to electrically stimulate a heart muscle or an autonomic neural target using stimulation parameters;
   receiving parameter values, wherein the received parameter values include parameter values for at least a respiration parameter and a heart sound parameter;
   using an algorithm to process the received parameter values; and
   changing the stimulation parameters based on the processed received parameter values.

2. The method of claim 1, wherein the received parameter values further include parameter values for a patient activity parameter.

3. The method of claim 1, wherein the therapy includes electrical stimulation of the heart muscle.

4. The method of claim 1, wherein the therapy includes electrical stimulation of the autonomic neural target.

5. The method of claim 1, wherein the received parameter values, processed using the algorithm, further include a heart rate variability (HRV) measurement.

6. The method of claim 1, wherein the received parameter values, processed using the algorithm, further include a heart rate turbulence (HRT) measurement.

7. The method of claim 1, wherein the received parameter values, processed using the algorithm, further include a blood pressure measurement.

8. The method of claim 1, wherein at least some of the parameter values are received from at least one of: a sensor, a physician input, a patient input, a patient history data source, a pharmaceutical data source, and a population/clinical study data source.

9. The method of claim 1, wherein the parameter values for the respiration parameter include a transthoracic impedance.

10. The method of claim 1, wherein the parameter values for the respiration parameter include a minute ventilation.

11. The method of claim 1, wherein the parameter values for the respiration parameter include a tidal volume.

12. The method of claim 1, wherein the received parameter values further include an exercise activity.

13. The method of claim 1, wherein the received parameter values further include a heart rate or a respiration rate.

14. A non-transitory machine-readable medium including instructions, which when executed by a machine, cause the machine to:
   deliver a therapy using an implantable device to electrically stimulate a heart muscle or an autonomic neural target using stimulation parameters;
   receive parameter values, wherein the received parameter values include parameter values for at least a respiration parameter and a heart sound parameter;
   use an algorithm to process the received parameter values; and
   change the stimulation parameters based on the processed received parameter values.

15. The non-transitory machine-readable medium of claim 14, wherein at least some of the parameter values are received from at least one of: a sensor, a physician input, a patient input data source, a patient history data source, a pharmaceutical data source, and a population/clinical study data source.

16. The non-transitory machine-readable medium of claim 14, wherein the received parameter values further include parameter values for a patient activity parameter.

17. A system, comprising:
   an implantable heart failure therapy delivery system configured to deliver a heart failure (HF) therapy to electrically stimulate a heart muscle or an autonomic neural target; and
   control circuitry operably connected to the therapy delivery system and configured to:
   receive parameter values, wherein the received parameter values include parameter values for at least a respiration parameter and a heart sound parameter;
   generate at least a first HF status index and a second HF status index from the received parameter values; and
   change the electrical stimulation based on the received parameter values.

18. The system of claim 17, wherein the control circuitry is configured to receive parameter values from one or more data source types selected from a group of data source types consisting of: a sensor data source type, a physician input data source type, a patient input data source type, a patient history data source type, a pharmaceutical data source type, and a population/clinical study data source type.

19. The system of claim 17, wherein the implantable heart failure therapy delivery system is configured to electrically stimulate the heart muscle to deliver the HF therapy.

20. The system of claim 17, wherein the implantable heart failure therapy delivery system is configured to electrically stimulate the autonomic neural target to deliver the HF therapy.

* * * * *